US008080643B2

(12) United States Patent
King et al.

(10) Patent No.: US 8,080,643 B2
(45) Date of Patent: Dec. 20, 2011

(54) HPV PRIMERS

(75) Inventors: Joseph J. King, Madison, WI (US);
Angela Hudson, Oregon, WI (US)

(73) Assignee: Third Wave Technologies, Inc., Madison, WI (US)

( * ) Notice: Subject to any disclaimer, the term of this patent is extended or adjusted under 35 U.S.C. 154(b) by 539 days.

(21) Appl. No.: 11/850,191

(22) Filed: Sep. 5, 2007

(65) Prior Publication Data
US 2008/0187919 A1    Aug. 7, 2008

Related U.S. Application Data

(60) Provisional application No. 60/842,301, filed on Sep. 5, 2006.

(51) Int. Cl.
*C07H 21/04* (2006.01)
*C12Q 1/68* (2006.01)
(52) U.S. Cl. ............... 536/23.1; 536/24.3; 435/6.1
(58) Field of Classification Search .................. None
See application file for complete search history.

(56) References Cited

U.S. PATENT DOCUMENTS

| | | |
|---|---|---|
| 4,551,270 A | 11/1985 | Danos et al. |
| 4,849,331 A | 7/1989 | Lorincz |
| 4,849,332 A | 7/1989 | Lorincz |
| 4,849,334 A | 7/1989 | Lorincz |
| 4,908,306 A | 3/1990 | Lorincz |
| 5,057,411 A | 10/1991 | Lancaster |
| 5,182,377 A | 1/1993 | Manos |
| 5,283,171 A | 2/1994 | Manos |
| 5,342,930 A | 8/1994 | Orth et al. |
| 5,364,758 A | 11/1994 | Meijer et al. |
| 5,411,857 A | 5/1995 | Beaudenon et al. |
| 5,447,839 A | 9/1995 | Bauer |
| 5,484,699 A | 1/1996 | Bouma |
| 5,501,947 A | 3/1996 | Emery |
| 5,527,898 A | 6/1996 | Bauer |
| 5,534,439 A | 7/1996 | Orth et al. |
| 5,554,538 A | 9/1996 | Cole et al. |
| 5,580,970 A | 12/1996 | Hendricks |
| 5,591,574 A | 1/1997 | Orth et al. |
| 5,614,402 A | 3/1997 | Dahlberg |
| 5,639,871 A | 6/1997 | Bauer |
| 5,643,715 A | 7/1997 | Lancaster |
| 5,648,459 A | 7/1997 | Cole et al. |
| 5,656,423 A | 8/1997 | Orth et al. |
| 5,665,535 A | 9/1997 | Orth et al. |
| 5,665,571 A | 9/1997 | Beaudenon et al. |
| 5,679,509 A | 10/1997 | Wheeler |
| 5,681,944 A | 10/1997 | Crooke |
| 5,705,627 A | 1/1998 | Manos |
| 5,712,092 A | 1/1998 | Orth |
| 5,783,412 A | 7/1998 | Morris |
| 5,795,763 A | 8/1998 | Dahlberg |
| 5,811,232 A | 9/1998 | Crooke |
| 5,824,466 A | 10/1998 | Orth et al. |
| 5,840,306 A | 11/1998 | Hofmann |
| 5,843,669 A | 12/1998 | Kaiser |
| 5,846,717 A | 12/1998 | Brow |
| 5,863,717 A | 1/1999 | Lancaster |
| 5,876,922 A | 3/1999 | Orth et al. |
| 5,888,724 A | 3/1999 | Silverstein |
| 5,952,487 A | 9/1999 | Philipp et al. |
| 5,958,674 A | 9/1999 | Beaudenon et al. |
| 5,981,173 A | 11/1999 | Orth et al. |
| 5,985,557 A | 11/1999 | Prudent |
| 5,994,069 A | 11/1999 | Hall |
| 6,001,567 A | 12/1999 | Brow |
| 6,001,983 A | 12/1999 | Benner |
| 6,045,993 A | 4/2000 | Mahony |
| 6,090,543 A | 7/2000 | Prudent |
| 6,107,086 A | 8/2000 | Cole et al. |
| 6,117,634 A | 9/2000 | Langmore |
| 6,127,164 A | 10/2000 | de Villiers et al. |
| 6,159,729 A | 12/2000 | Hofmann et al. |
| 6,183,960 B1 | 2/2001 | Lizardi |
| 6,194,149 B1 | 2/2001 | Neri |
| 6,197,557 B1 | 3/2001 | Makarov |
| 6,210,884 B1 | 4/2001 | Lizardi |
| 6,218,104 B1 | 4/2001 | Morris |
| 6,228,577 B1 | 5/2001 | Mahony |
| 6,235,502 B1 | 5/2001 | Weissman |
| 6,242,250 B1 | 6/2001 | Cole |
| 6,265,154 B1 | 7/2001 | Kroeger |
| 6,344,314 B2 | 2/2002 | Cole et al. |
| 6,352,825 B1 | 3/2002 | Meijer et al. |
| 6,420,106 B1 | 7/2002 | Gyllensten |
| 6,458,940 B2 | 10/2002 | Robert |
| 6,482,588 B1 * | 11/2002 | Van Doorn et al. ............... 435/5 |
| 6,503,704 B1 | 1/2003 | Mahony |
| 6,509,149 B2 | 1/2003 | Roberts |
| 6,511,805 B1 | 1/2003 | Gocke |
| 6,583,278 B1 | 6/2003 | Carter |
| 6,613,557 B1 | 9/2003 | Frazer |
| 6,649,167 B2 | 11/2003 | Hallek |
| 6,827,933 B2 | 12/2004 | Orth et al. |
| 6,858,412 B2 | 2/2005 | Willis et al. |
| 7,195,871 B2 | 3/2007 | Lyamichev et al. |
| 2002/0155427 A1 | 10/2002 | Cohenford et al. |
| 2003/0152942 A1 | 8/2003 | Fors et al. |
| 2004/0170982 A1 | 9/2004 | Morris et al. |

(Continued)

OTHER PUBLICATIONS

Lorincz et al. Cloning and partial DNA sequencing of two new human papillomavirus types associated with condylomas and low-grade cervical neoplasia. J. Virol. (1989) vol. 63, No. 6, pp. 2829-2834.*
Lorincz et al. Human papillomavirus type 43 complete genome. (2005) GenBank accession No. AJ620205.*

(Continued)

*Primary Examiner* — Kenneth R. Horlick
*Assistant Examiner* — David Thomas
(74) *Attorney, Agent, or Firm* — Casimir Jones, S.C.

(57) ABSTRACT

The present invention provides methods, kits, and compositions related to human papillomavirus (HPV) primers, which may be used, for example, in nucleic acid detection assays for use in basic research, clinical research, and for the development of clinical detection assays.

10 Claims, No Drawings

OTHER PUBLICATIONS

Schweitzer, et al. "Hydrophobic, Non-Hydrogen-Bonding Bases and Base Pairs in DNA" J. Am. Chem. Soc., 1995, 117, 1863-1872.
Vernon, et al. "Bioelectric DNA detection of human papillomaviruses using eSensor: a model system for detection of multiple pathogens" BMC Infectious Diseases, vol. 3: 12 pp. 1-9, Jun. 2003.
Wallboomers, et al. "Human papillomavirus is a necessary cause of invasive cervical cancer worldwide" 1999 J Pathol. 189 pp. 12-19.
Wright, et al. "2001 Consensus Guidelines for the management of women with cervical cytological abnormalities" JAMA, vol. 287 pp. 2120-2129 (2002).
Wright, et al. "Adding a test for human papillomavirus DNA to cervical-cancer screening." 2003 Engl. J. Med. 348 pp. 489-490.
Wright, et al. "HPV DNA testing of self-collected vaginal samples compared with cytologic screening to detect cervical cancer" JAMA, vol. 283, pp. 81-86 (2000).
Allawi, et al. "Thermodynamics and NMR of internal G.T mismatches in DNA" Biochemistry 36, 10581-94 (1997).
Anderson, et al. "Quantitative Filter Hybridization" in Nucleic Acid Hybridization, pp. 73-111 (1985).
Bosch, et al. "The casual relation between human papillomavirus and cervical cancer" J Clin. Pathol. 2002; 55:244-65.
Burd, et al. "Human papillomavirus and cervical cancer." 2003 Clin Microbiol Rev. 16 pp. 1-17.
Campo, et al. Molecular Cloning of Bovine Papillomavirus Genomes and Comparison of Their Sequence Homologies by Heteroduplex Mapping. J. gen. Virol. (1982), 63, 255-264.
Clavel, et al. "Human papillomavirus testing in primary screening for the detection of high-grade cervical lesions: a study of 7932 women" 2001. Br J Cancer, vol. 84, pp. 1616-1623.
Coggins, et al. "The Genomes of Bovine Papillomaviruses Types 3 and 4 are Colinear" J. gen. Viral. (1983), 64, 2771-2776.
Crum, et al. "Human Papillomavirus Type 16 and Early Cervical Neoplasia. The New England Journal of Medicine" Apr. 1984; 310(14):880-883.
Danos, et al. "Molecular Cloning, Refined Physical Map and Heterogeneity of Methylation Sites of Papilloma Virus Type 1a DNA" Eur. J. Biochem. (1980),109,457-461.
Doty, et al. "Strand Separation and Specific Recombination in Deoxyribonucleic Acids: Physical Chemical Studies" Proc. Natl. Acad. Sci. USA 46:461-76 (1960).
Fahey, et al. "Meta-analysis of Pap test accuracy" Am J Epidemiol. 1995;141:680-9.
Franco, et al. "Cervical cancer: epidemiology, prevention and the role of human papillomavirus infection" CMAJ, vol. 164, pp. 1017-1025 (2001).
Gissmann "Human Papillomavirus DNA in Genital Tumours" IARC Sci. Publ. 1984, 63, 405-411.
Gissmann, et al. Presence of Human Papillomavirus in Genital Tumors. The Journal of Investigative Dermatology. (1984), 83, 26s-28s.
Gravitt, et al. "Improved amplification of genital human papillomaviruses" 2000 J. Clin. Microbiol. 38(1) pp. 357-361.
Hall, et al. "Sensitive detection of DNA polymorphisms by the serial invasive signal amplification reaction." 2000 PNAS USA 97 pp. 8272.
Howley "The Human Papillomaviruses" Arch Pathol Lab Med. (1982), 106,429-432.
Hutchinson, et al. "Utility of liquid-based cytology for cervical carcinoma screening: results of a population-based study conducted in a region of Costa Rica with a high incidence of cervical carcinoma" 1999, Cancer, vol. 87, pp. 48-55.
Hybrid Capture II (HCII) test, Digene, Gaithersburg, MD, (2007).
Ikenberg, et al. "Human Papillomavirus Type-16-Related DNA in Genital Bowen's Disease and in Bowenoid Papulosis" Int. J. Cancer. (1983), 32, 563-565.
Kleter, et al. "Development and clinical evaluation of a highly sensitive PCR-reverse hybridization line probe assay for detection and identification of anogenital human papillomavirus" Journal of Clinical Microbiology, vol. 37, No. 8, pp. 2508-2517, Aug. 1999.
Kong, et al. "Synthesis and duplex stability of oligonucleotides containing cytosine-thymine analogues" Nucleic Acids Res., 1989, 17, 10373-10383.
Kong, et al. "Synthesis of oligodeoxyribonucleotides containing degenerate bases and their use as primers in the polymerase chain reaction" Nucleic Acids Res., 1992, 20, 5149-5152.
Koutsky, et al. "A controlled trial of a human papillomavirus type 16 vaccine." 2002 NEJM 347 pp. 1645-1651.
Lancaster "Human Papillomavirus: Detection of Viral DNA Sequences and Evidence for Molecular Heterogeneity in Metaplasias and Dysplasias of the Uterine Cervix" Intervirology. (1983), 20, 202-212.
Lin, et al. "Synthesis and Duplex Stability of Oligonucleotides Containing Cytosine-Thymine Analogues" Nucleic Acids Res., 1989, 17, 10373-10383.
Lin, et al. "Synthesis of Oligodeoxyribonucleotides Containing Degenerate Bases and Their Use as Primers in the Polymerase Chain Reaction" Nucleic Acids Research. (1992), 20(19), 5149-5152.
Lorincz "Hybrid Capture method for detection of human papillomavirus DNA in clinical specimens: a tool for clinical management of equivocal Pap smears and for population screening" J Obstet Gynaecol Res. 1996;22:629-36.
Lorincz, et al. "Cloning and partial DNA sequencing of two new human papillomavirus types associated with condylomas and lowgrade cervical neoplasia" J. Virol. (1989) vol. 63, No. 6, pp. 2829-2834.
Lorincz, et al. "Human papillomavirus DNA testing as an adjunct to cytology in cervical screening programs" Arch Pathol Lab Med. 2003;127:959-68.
Lorincz, et al. "Human papillomavirus type 43 complete genome" (2005) GenBank accession No. AJ620205.
Lyamichev, et al. "Polymorphism identification and quantitative detection of genomic DNA by invasive cleavage of oligonucleotide probes." 1999 Nat. Biotech. 17 pp. 292-296.
Marmur, et al. "Strand Separation and Specific Recombination in Deoxyribonucleic Acids: Biological Studies" Proc. Natl. Acad. Sci. USA 46:453-61 (1960).
Munoz "Epidemiologic classification of human papillomavirus types associated with cervical cancer" 2003 N Engl J. Med 348 pp. 518-527.
Munoz, et al. "The causal link between human papillomavirus and invasive cervical cancer: a population-based case-control study in Colombia and Spain" Int J Cancer 1992;52:743-9.
Myers, et al. "Setting the target for a better cervical screening test: characteristics of a cost-effective test for cervical neoplasia screening" Obstet Gynecol. 2000;96:645-52.
Nanda, et al. "Accuracy of the Papanicolaou test in screening for and follow-up of cervical cytologic abnormalities: a systematic review" 2000. Ann Intern Med 132:810-9.
Okagaki, et al. Identification of Human Papillomavirus DNA in Cervical and VaginalIntraepithelial Neoplasia with Molecularly Cloned Virus-Specific DNA Probes. International Journal of Gynecological Pathology. (1983),2,153-159.
Orth, et al. "Identification of Papillomaviruses in Butchers' Warts" The Journal of Investigative Dermatology. 1981; 76 (2): 97-102.
Ostrow, et al. "Identification of three distinct papillomavirus genomes in a single patient with epidermodysplasia verruciformis" J. Am. Acad. Dermatol. (1983) 8,398-404.
Ostrow, et al. "Molecular Cloning and Characterization of a Unique Type of Human Papillomavirus from an Immune Deficient Patient" The Journal of Investigative Dermatology. Apr. 1984 82(4), p. 362-366.
Pfister, et al. Characterization of a Human Papillomavirus From Epidermodysplasia Verruciform is Lesions of a Patient From Upper-Volta. Int. J. Cancer. (1981), 27, 645-650.
Pfister, et al. "Characterization of Human Papillomavirus 3 in Warts of a Renal Allograft Patient" The Journal of Investigative Dermatology. 1979; 73(5):349-353.
Poljak, et al. "Hybrid Capture II HPV Test detects at least 15 human papillomavirus genotypes not included in its current high-risk probe cocktail" Journal of Clinical Virology, vol. 25, pp. 889-897, 2002.
Potter, et al. "Nucleotide Sequence of Bovine Papillomavirus Type 2 Late Region" J. Gen. Viral. (1985), 66,187-193.

Qureshi, et al. "Role of HPV DNA testing in predicting cervical intraepithelial lesions: comparison of HC HPV and ISH HPV." 2003 Diagn. Cytopathol. 29 pp. 149-155.

Report of the Gynecologic Cancers Progress Review Group, Nov. 2001, National Cancer Institute.

Reynaldo, et al. "The Kinetics of Oligonucleotide Replacements" J. Mol. Biol. (2000), 297, 511-520.

Rossi, et al. "An Alternate Method for Synthesis of Double-stranded DNA Segments" The Journal of Biological Chemistry. (1982), 257(16), 9226-9229.

Schweitzer, et al. "Aromatic Nonpolar Nucleosides as Hydrophobic Isosteres of Pyrimidine and Purine Nucleosides" J. Org. Chem., 1994, 59, 7238-7242.

* cited by examiner

SEQUENCE LISTING

<160> NUMBER OF SEQ ID NOS: 154

<210> SEQ ID NO 1
<211> LENGTH: 20
<212> TYPE: DNA
<213> ORGANISM: Artificial
<220> FEATURE:
<223> OTHER INFORMATION: Synthetic

<400> SEQUENCE: 1
tcgcagcacc aatctttctg                                           20

<210> SEQ ID NO 2
<211> LENGTH: 20
<212> TYPE: DNA
<213> ORGANISM: Artificial
<220> FEATURE:
<223> OTHER INFORMATION: Synthetic

<400> SEQUENCE: 2
caccaatctt tctgtgtgtg                                           20

<210> SEQ ID NO 3
<211> LENGTH: 20
<212> TYPE: DNA
<213> ORGANISM: Artificial
<220> FEATURE:
<223> OTHER INFORMATION: Synthetic

<400> SEQUENCE: 3
gtttaactgg cggtgcggtg                                           20

<210> SEQ ID NO 4
<211> LENGTH: 20
<212> TYPE: DNA
<213> ORGANISM: Artificial
<220> FEATURE:
<223> OTHER INFORMATION: Synthetic

<400> SEQUENCE: 4
gttacagcag cagattgaac                                           20

<210> SEQ ID NO 5
<211> LENGTH: 19
<212> TYPE: DNA
<213> ORGANISM: Artificial
<220> FEATURE:
<223> OTHER INFORMATION: Synthetic

<400> SEQUENCE: 5
ataaccttaa ctgcagacg                                            19

<210> SEQ ID NO 6
<211> LENGTH: 19
<212> TYPE: DNA
<213> ORGANISM: Artificial
<220> FEATURE:
<223> OTHER INFORMATION: Synthetic

<400> SEQUENCE: 6
gaggcacact agaagatac                                            19

<210> SEQ ID NO 7
<211> LENGTH: 29
<212> TYPE: DNA

```
<213> ORGANISM: Artificial
<220> FEATURE:
<223> OTHER INFORMATION: Synthetic

<400> SEQUENCE: 7
gaatatgatt tacagtttat ttttcaact                                    29

<210> SEQ ID NO 8
<211> LENGTH: 20
<212> TYPE: DNA
<213> ORGANISM: Artificial
<220> FEATURE:
<223> OTHER INFORMATION: Synthetic

<400> SEQUENCE: 8
tgtgctgcca tatctacttc                                              20

<210> SEQ ID NO 9
<211> LENGTH: 22
<212> TYPE: DNA
<213> ORGANISM: Artificial
<220> FEATURE:
<223> OTHER INFORMATION: Synthetic

<400> SEQUENCE: 9
cctataagta tcttctagtg tg                                           22

<210> SEQ ID NO 10
<211> LENGTH: 20
<212> TYPE: DNA
<213> ORGANISM: Artificial
<220> FEATURE:
<223> OTHER INFORMATION: Synthetic

<400> SEQUENCE: 10
atcttctagt gtgcctcctg                                              20

<210> SEQ ID NO 11
<211> LENGTH: 22
<212> TYPE: DNA
<213> ORGANISM: Artificial
<220> FEATURE:
<223> OTHER INFORMATION: Synthetic

<400> SEQUENCE: 11
atatgtgctt ctacacagtc tc                                           22

<210> SEQ ID NO 12
<211> LENGTH: 22
<212> TYPE: DNA
<213> ORGANISM: Artificial
<220> FEATURE:
<223> OTHER INFORMATION: Synthetic

<400> SEQUENCE: 12
ccaatttaac aatatgtgct tc                                           22

<210> SEQ ID NO 13
<211> LENGTH: 20
<212> TYPE: DNA
<213> ORGANISM: Artificial
<220> FEATURE:
<223> OTHER INFORMATION: Synthetic

<400> SEQUENCE: 13
atccaccaaa ctagtagttg                                              20
```

```
<210> SEQ ID NO 14
<211> LENGTH: 20
<212> TYPE: DNA
<213> ORGANISM: Artificial
<220> FEATURE:
<223> OTHER INFORMATION: Synthetic

<400> SEQUENCE: 14
ttgacaggta atagcaacag                                                    20

<210> SEQ ID NO 15
<211> LENGTH: 19
<212> TYPE: DNA
<213> ORGANISM: Artificial
<220> FEATURE:
<223> OTHER INFORMATION: Synthetic

<400> SEQUENCE: 15
caattgcaaa cagtgatac                                                     19

<210> SEQ ID NO 16
<211> LENGTH: 22
<212> TYPE: DNA
<213> ORGANISM: Artificial
<220> FEATURE:
<223> OTHER INFORMATION: Synthetic

<400> SEQUENCE: 16
agagtattta agacatggtg ag                                                 22

<210> SEQ ID NO 17
<211> LENGTH: 21
<212> TYPE: DNA
<213> ORGANISM: Artificial
<220> FEATURE:
<223> OTHER INFORMATION: Synthetic

<400> SEQUENCE: 17
gtgtggtcaa tccaaaattc c                                                  21

<210> SEQ ID NO 18
<211> LENGTH: 20
<212> TYPE: DNA
<213> ORGANISM: Artificial
<220> FEATURE:
<223> OTHER INFORMATION: Synthetic

<400> SEQUENCE: 18
gagggaggtg tggtcaatcc                                                    20

<210> SEQ ID NO 19
<211> LENGTH: 17
<212> TYPE: DNA
<213> ORGANISM: Artificial
<220> FEATURE:
<223> OTHER INFORMATION: Synthetic

<400> SEQUENCE: 19
ggaggtgtgg tcaatcc                                                       17

<210> SEQ ID NO 20
<211> LENGTH: 21
<212> TYPE: DNA
<213> ORGANISM: Artificial
<220> FEATURE:
<223> OTHER INFORMATION: Synthetic
```

-continued

```
<400> SEQUENCE: 20
ctaatatgac tttatgcaca c                                              21

<210> SEQ ID NO 21
<211> LENGTH: 21
<212> TYPE: DNA
<213> ORGANISM: Artificial
<220> FEATURE:
<223> OTHER INFORMATION: Synthetic

<400> SEQUENCE: 21
atatgacttt atgcacacaa g                                              21

<210> SEQ ID NO 22
<211> LENGTH: 22
<212> TYPE: DNA
<213> ORGANISM: Artificial
<220> FEATURE:
<223> OTHER INFORMATION: Synthetic

<400> SEQUENCE: 22
tataggtatc ctgtaaacta gc                                             22

<210> SEQ ID NO 23
<211> LENGTH: 20
<212> TYPE: DNA
<213> ORGANISM: Artificial
<220> FEATURE:
<223> OTHER INFORMATION: Synthetic

<400> SEQUENCE: 23
gacacgtaat agcctgagag                                                20

<210> SEQ ID NO 24
<211> LENGTH: 23
<212> TYPE: DNA
<213> ORGANISM: Artificial
<220> FEATURE:
<223> OTHER INFORMATION: Synthetic

<400> SEQUENCE: 24
tataggtatc ctgtaaacta gca                                            23

<210> SEQ ID NO 25
<211> LENGTH: 21
<212> TYPE: DNA
<213> ORGANISM: Artificial
<220> FEATURE:
<223> OTHER INFORMATION: Synthetic

<400> SEQUENCE: 25
gtctgtgtgt tctgctgtgt c                                              21

<210> SEQ ID NO 26
<211> LENGTH: 22
<212> TYPE: DNA
<213> ORGANISM: Artificial
<220> FEATURE:
<223> OTHER INFORMATION: Synthetic

<400> SEQUENCE: 26
ttaaggaata tttaaggcat gg                                             22

<210> SEQ ID NO 27
<211> LENGTH: 20
<212> TYPE: DNA
```

```
<213> ORGANISM: Artificial
<220> FEATURE:
<223> OTHER INFORMATION: Synthetic

<400> SEQUENCE: 27
ggatcatctt taggttttgg                                                    20

<210> SEQ ID NO 28
<211> LENGTH: 22
<212> TYPE: DNA
<213> ORGANISM: Artificial
<220> FEATURE:
<223> OTHER INFORMATION: Synthetic

<400> SEQUENCE: 28
ctgggttttt gacaagttac ag                                                 22

<210> SEQ ID NO 29
<211> LENGTH: 21
<212> TYPE: DNA
<213> ORGANISM: Artificial
<220> FEATURE:
<223> OTHER INFORMATION: Synthetic

<400> SEQUENCE: 29
tatagagtct tccatacctt c                                                  21

<210> SEQ ID NO 30
<211> LENGTH: 21
<212> TYPE: DNA
<213> ORGANISM: Artificial
<220> FEATURE:
<223> OTHER INFORMATION: Synthetic

<400> SEQUENCE: 30
accaacttta cattatctac c                                                  21

<210> SEQ ID NO 31
<211> LENGTH: 21
<212> TYPE: DNA
<213> ORGANISM: Artificial
<220> FEATURE:
<223> OTHER INFORMATION: Synthetic

<400> SEQUENCE: 31
cagatggtgg aggagctaca g                                                  21

<210> SEQ ID NO 32
<211> LENGTH: 21
<212> TYPE: DNA
<213> ORGANISM: Artificial
<220> FEATURE:
<223> OTHER INFORMATION: Synthetic

<400> SEQUENCE: 32
aacattccaa aactttagac c                                                  21

<210> SEQ ID NO 33
<211> LENGTH: 20
<212> TYPE: DNA
<213> ORGANISM: Artificial
<220> FEATURE:
<223> OTHER INFORMATION: Synthetic

<400> SEQUENCE: 33
aatttaacat tatgtgcctc                                                    20
```

<210> SEQ ID NO 34
<211> LENGTH: 22
<212> TYPE: DNA
<213> ORGANISM: Artificial
<220> FEATURE:
<223> OTHER INFORMATION: Synthetic

<400> SEQUENCE: 34
ctaatttaac attatgtgcc tc                                              22

<210> SEQ ID NO 35
<211> LENGTH: 21
<212> TYPE: DNA
<213> ORGANISM: Artificial
<220> FEATURE:
<223> OTHER INFORMATION: Synthetic

<400> SEQUENCE: 35
ggtaacagca actgattgca c                                               21

<210> SEQ ID NO 36
<211> LENGTH: 21
<212> TYPE: DNA
<213> ORGANISM: Artificial
<220> FEATURE:
<223> OTHER INFORMATION: Synthetic

<400> SEQUENCE: 36
aacttgtagt aggtggtgga g                                               21

<210> SEQ ID NO 37
<211> LENGTH: 22
<212> TYPE: DNA
<213> ORGANISM: Artificial
<220> FEATURE:
<223> OTHER INFORMATION: Synthetic

<400> SEQUENCE: 37
tttactccaa gtaactttaa gc                                              22

<210> SEQ ID NO 38
<211> LENGTH: 20
<212> TYPE: DNA
<213> ORGANISM: Artificial
<220> FEATURE:
<223> OTHER INFORMATION: Synthetic

<400> SEQUENCE: 38
aatcagcttt ttattacctg                                                 20

<210> SEQ ID NO 39
<211> LENGTH: 23
<212> TYPE: DNA
<213> ORGANISM: Artificial
<220> FEATURE:
<223> OTHER INFORMATION: Synthetic

<400> SEQUENCE: 39
ctccaagtaa ctttaagcaa tat                                             23

<210> SEQ ID NO 40
<211> LENGTH: 20
<212> TYPE: DNA
<213> ORGANISM: Artificial
<220> FEATURE:
<223> OTHER INFORMATION: Synthetic

```
<400> SEQUENCE: 40
catcctccaa actagcagac                                              20

<210> SEQ ID NO 41
<211> LENGTH: 21
<212> TYPE: DNA
<213> ORGANISM: Artificial
<220> FEATURE:
<223> OTHER INFORMATION: Synthetic

<400> SEQUENCE: 41
cgttccttta aatcaacatc c                                            21

<210> SEQ ID NO 42
<211> LENGTH: 22
<212> TYPE: DNA
<213> ORGANISM: Artificial
<220> FEATURE:
<223> OTHER INFORMATION: Synthetic

<400> SEQUENCE: 42
acatcccaaa atttatattt gg                                           22

<210> SEQ ID NO 43
<211> LENGTH: 20
<212> TYPE: DNA
<213> ORGANISM: Artificial
<220> FEATURE:
<223> OTHER INFORMATION: Synthetic

<400> SEQUENCE: 43
aattttaagg aataccttcg                                              20

<210> SEQ ID NO 44
<211> LENGTH: 22
<212> TYPE: DNA
<213> ORGANISM: Artificial
<220> FEATURE:
<223> OTHER INFORMATION: Synthetic

<400> SEQUENCE: 44
aattttaagg aataccttcg tc                                           22

<210> SEQ ID NO 45
<211> LENGTH: 18
<212> TYPE: DNA
<213> ORGANISM: Artificial
<220> FEATURE:
<223> OTHER INFORMATION: Synthetic

<400> SEQUENCE: 45
catgacttta tgtgctga                                                18

<210> SEQ ID NO 46
<211> LENGTH: 20
<212> TYPE: DNA
<213> ORGANISM: Artificial
<220> FEATURE:
<223> OTHER INFORMATION: Synthetic

<400> SEQUENCE: 46
aacatgactt tatgtgctga                                              20

<210> SEQ ID NO 47
<211> LENGTH: 23
<212> TYPE: DNA
```

<213> ORGANISM: Artificial
<220> FEATURE:
<223> OTHER INFORMATION: Synthetic

<400> SEQUENCE: 47
gaaaatttta aggaatacct tcg                                          23

<210> SEQ ID NO 48
<211> LENGTH: 21
<212> TYPE: DNA
<213> ORGANISM: Artificial
<220> FEATURE:
<223> OTHER INFORMATION: Synthetic

<400> SEQUENCE: 48
ccaaagatgc agacggtggt g                                            21

<210> SEQ ID NO 49
<211> LENGTH: 22
<212> TYPE: DNA
<213> ORGANISM: Artificial
<220> FEATURE:
<223> OTHER INFORMATION: Synthetic

<400> SEQUENCE: 49
aatctgtatg tgtcctccaa ag                                           22

<210> SEQ ID NO 50
<211> LENGTH: 20
<212> TYPE: DNA
<213> ORGANISM: Artificial
<220> FEATURE:
<223> OTHER INFORMATION: Synthetic

<400> SEQUENCE: 50
atgcacgaaa aattaatcag                                              20

<210> SEQ ID NO 51
<211> LENGTH: 22
<212> TYPE: DNA
<213> ORGANISM: Artificial
<220> FEATURE:
<223> OTHER INFORMATION: Synthetic

<400> SEQUENCE: 51
cagttaagta aatatgatgc ac                                           22

<210> SEQ ID NO 52
<211> LENGTH: 20
<212> TYPE: DNA
<213> ORGANISM: Artificial
<220> FEATURE:
<223> OTHER INFORMATION: Synthetic

<400> SEQUENCE: 52
gtcctgtttt tctgttggtg                                              20

<210> SEQ ID NO 53
<211> LENGTH: 20
<212> TYPE: DNA
<213> ORGANISM: Artificial
<220> FEATURE:
<223> OTHER INFORMATION: Synthetic

<400> SEQUENCE: 53
tctatattta tcttctaggc                                              20

```
<210> SEQ ID NO 54
<211> LENGTH: 21
<212> TYPE: DNA
<213> ORGANISM: Artificial
<220> FEATURE:
<223> OTHER INFORMATION: Synthetic

<400> SEQUENCE: 54
ctaatatgac attatgcact g                                       21

<210> SEQ ID NO 55
<211> LENGTH: 22
<212> TYPE: DNA
<213> ORGANISM: Artificial
<220> FEATURE:
<223> OTHER INFORMATION: Synthetic

<400> SEQUENCE: 55
acagtttgtt tttcagcttt gc                                      22

<210> SEQ ID NO 56
<211> LENGTH: 22
<212> TYPE: DNA
<213> ORGANISM: Artificial
<220> FEATURE:
<223> OTHER INFORMATION: Synthetic

<400> SEQUENCE: 56
ttggcaagta atagcctggg ag                                      22

<210> SEQ ID NO 57
<211> LENGTH: 17
<212> TYPE: DNA
<213> ORGANISM: Artificial
<220> FEATURE:
<223> OTHER INFORMATION: Synthetic

<400> SEQUENCE: 57
ctgggaggta acaaatc                                            17

<210> SEQ ID NO 58
<211> LENGTH: 23
<212> TYPE: DNA
<213> ORGANISM: Artificial
<220> FEATURE:
<223> OTHER INFORMATION: Synthetic

<400> SEQUENCE: 58
gaggtaacaa atctatatgt gtc                                     23

<210> SEQ ID NO 59
<211> LENGTH: 17
<212> TYPE: DNA
<213> ORGANISM: Artificial
<220> FEATURE:
<223> OTHER INFORMATION: Synthetic

<400> SEQUENCE: 59
tgctgttttt tggcaag                                            17

<210> SEQ ID NO 60
<211> LENGTH: 20
<212> TYPE: DNA
<213> ORGANISM: Artificial
<220> FEATURE:
<223> OTHER INFORMATION: Synthetic
```

```
<400> SEQUENCE: 60
gcagctaaaa gcacattaac                                               20

<210> SEQ ID NO 61
<211> LENGTH: 22
<212> TYPE: DNA
<213> ORGANISM: Artificial
<220> FEATURE:
<223> OTHER INFORMATION: Synthetic

<400> SEQUENCE: 61
cgtgaaatca atcaatacct tc                                            22

<210> SEQ ID NO 62
<211> LENGTH: 21
<212> TYPE: DNA
<213> ORGANISM: Artificial
<220> FEATURE:
<223> OTHER INFORMATION: Synthetic

<400> SEQUENCE: 62
tcccaaaact tatatttagc c                                             21

<210> SEQ ID NO 63
<211> LENGTH: 22
<212> TYPE: DNA
<213> ORGANISM: Artificial
<220> FEATURE:
<223> OTHER INFORMATION: Synthetic

<400> SEQUENCE: 63
tacctatatt tatcctctaa gc                                            22

<210> SEQ ID NO 64
<211> LENGTH: 20
<212> TYPE: DNA
<213> ORGANISM: Artificial
<220> FEATURE:
<223> OTHER INFORMATION: Synthetic

<400> SEQUENCE: 64
aatatgttag gcatgttgag                                               20

<210> SEQ ID NO 65
<211> LENGTH: 22
<212> TYPE: DNA
<213> ORGANISM: Artificial
<220> FEATURE:
<223> OTHER INFORMATION: Synthetic

<400> SEQUENCE: 65
ggaatatgtt aggcatgttg ag                                            22

<210> SEQ ID NO 66
<211> LENGTH: 21
<212> TYPE: DNA
<213> ORGANISM: Artificial
<220> FEATURE:
<223> OTHER INFORMATION: Synthetic

<400> SEQUENCE: 66
atctacaaga ctagcagatg g                                             21

<210> SEQ ID NO 67
<211> LENGTH: 20
<212> TYPE: DNA
```

```
<213> ORGANISM: Artificial
<220> FEATURE:
<223> OTHER INFORMATION: Synthetic

<400> SEQUENCE: 67
tatgtatcta caagactagc                                                  20

<210> SEQ ID NO 68
<211> LENGTH: 22
<212> TYPE: DNA
<213> ORGANISM: Artificial
<220> FEATURE:
<223> OTHER INFORMATION: Synthetic

<400> SEQUENCE: 68
actaacatga ctttatgtgc tg                                               22

<210> SEQ ID NO 69
<211> LENGTH: 24
<212> TYPE: DNA
<213> ORGANISM: Artificial
<220> FEATURE:
<223> OTHER INFORMATION: Synthetic

<400> SEQUENCE: 69
cactaacatg actttatgtg ctga                                             24

<210> SEQ ID NO 70
<211> LENGTH: 17
<212> TYPE: DNA
<213> ORGANISM: Artificial
<220> FEATURE:
<223> OTHER INFORMATION: Synthetic

<400> SEQUENCE: 70
cgcagtacaa atatgtc                                                     17

<210> SEQ ID NO 71
<211> LENGTH: 19
<212> TYPE: DNA
<213> ORGANISM: Artificial
<220> FEATURE:
<223> OTHER INFORMATION: Synthetic

<400> SEQUENCE: 71
gctgccatat ctacttcag                                                   19

<210> SEQ ID NO 72
<211> LENGTH: 17
<212> TYPE: DNA
<213> ORGANISM: Artificial
<220> FEATURE:
<223> OTHER INFORMATION: Synthetic

<400> SEQUENCE: 72
agtacctacg acatggg                                                     17

<210> SEQ ID NO 73
<211> LENGTH: 25
<212> TYPE: DNA
<213> ORGANISM: Artificial
<220> FEATURE:
<223> OTHER INFORMATION: Synthetic

<400> SEQUENCE: 73
attttaagga atatttaagg catgg                                            25
```

<210> SEQ ID NO 74
<211> LENGTH: 22
<212> TYPE: DNA
<213> ORGANISM: Artificial
<220> FEATURE:
<223> OTHER INFORMATION: Synthetic

<400> SEQUENCE: 74
gaatatttaa ggcatggtga ag                                    22

<210> SEQ ID NO 75
<211> LENGTH: 19
<212> TYPE: DNA
<213> ORGANISM: Artificial
<220> FEATURE:
<223> OTHER INFORMATION: Synthetic

<400> SEQUENCE: 75
atatgttagg catgttgag                                        19

<210> SEQ ID NO 76
<211> LENGTH: 17
<212> TYPE: DNA
<213> ORGANISM: Artificial
<220> FEATURE:
<223> OTHER INFORMATION: Synthetic

<400> SEQUENCE: 76
gtgcttctac acagtct                                          17

<210> SEQ ID NO 77
<211> LENGTH: 21
<212> TYPE: DNA
<213> ORGANISM: Artificial
<220> FEATURE:
<223> OTHER INFORMATION: Synthetic

<400> SEQUENCE: 77
aatatgtgct tctacacagt c                                     21

<210> SEQ ID NO 78
<211> LENGTH: 23
<212> TYPE: DNA
<213> ORGANISM: Artificial
<220> FEATURE:
<223> OTHER INFORMATION: Synthetic

<400> SEQUENCE: 78
gcatccgtaa ctacatcttc cac                                   23

<210> SEQ ID NO 79
<211> LENGTH: 24
<212> TYPE: DNA
<213> ORGANISM: Artificial
<220> FEATURE:
<223> OTHER INFORMATION: Synthetic

<400> SEQUENCE: 79
cgtaactaca tcttccacat acac                                  24

<210> SEQ ID NO 80
<211> LENGTH: 19
<212> TYPE: DNA
<213> ORGANISM: Artificial
<220> FEATURE:
<223> OTHER INFORMATION: Synthetic

<400> SEQUENCE: 80
gcctgtgact gcacatacc					19

<210> SEQ ID NO 81
<211> LENGTH: 20
<212> TYPE: DNA
<213> ORGANISM: Artificial
<220> FEATURE:
<223> OTHER INFORMATION: Synthetic

<400> SEQUENCE: 81
catttggggg aggcgataac					20

<210> SEQ ID NO 82
<211> LENGTH: 22
<212> TYPE: DNA
<213> ORGANISM: Artificial
<220> FEATURE:
<223> OTHER INFORMATION: Synthetic

<400> SEQUENCE: 82
acacgcagta caaatatgac ac					22

<210> SEQ ID NO 83
<211> LENGTH: 22
<212> TYPE: DNA
<213> ORGANISM: Artificial
<220> FEATURE:
<223> OTHER INFORMATION: Synthetic

<400> SEQUENCE: 83
tgtgcatctg tgtctaaatc tg					22

<210> SEQ ID NO 84
<211> LENGTH: 22
<212> TYPE: DNA
<213> ORGANISM: Artificial
<220> FEATURE:
<223> OTHER INFORMATION: Synthetic

<400> SEQUENCE: 84
catttggtgg aggcgataaa cc					22

<210> SEQ ID NO 85
<211> LENGTH: 21
<212> TYPE: DNA
<213> ORGANISM: Artificial
<220> FEATURE:
<223> OTHER INFORMATION: Synthetic

<400> SEQUENCE: 85
acctcccaaa aactcatatc c					21

<210> SEQ ID NO 86
<211> LENGTH: 22
<212> TYPE: DNA
<213> ORGANISM: Artificial
<220> FEATURE:
<223> OTHER INFORMATION: Synthetic

<400> SEQUENCE: 86
cttaccatta gtacattatc tg					22

<210> SEQ ID NO 87
<211> LENGTH: 17
<212> TYPE: DNA

-continued

```
<213> ORGANISM: Artificial
<220> FEATURE:
<223> OTHER INFORMATION: Synthetic

<400> SEQUENCE: 87
gacaggtagt agcagag                                                        17

<210> SEQ ID NO 88
<211> LENGTH: 19
<212> TYPE: DNA
<213> ORGANISM: Artificial
<220> FEATURE:
<223> OTHER INFORMATION: Synthetic

<400> SEQUENCE: 88
ctttgtgtgc cactgcaac                                                      19

<210> SEQ ID NO 89
<211> LENGTH: 25
<212> TYPE: DNA
<213> ORGANISM: Artificial
<220> FEATURE:
<223> OTHER INFORMATION: Synthetic

<400> SEQUENCE: 89
gcaacatctg gtgatacata tacag                                               25

<210> SEQ ID NO 90
<211> LENGTH: 20
<212> TYPE: DNA
<213> ORGANISM: Artificial
<220> FEATURE:
<223> OTHER INFORMATION: Synthetic

<400> SEQUENCE: 90
ggcgttgtta ccttagcctg                                                     20

<210> SEQ ID NO 91
<211> LENGTH: 22
<212> TYPE: DNA
<213> ORGANISM: Artificial
<220> FEATURE:
<223> OTHER INFORMATION: Synthetic

<400> SEQUENCE: 91
acctcccaaa accaaaagtc tg                                                  22

<210> SEQ ID NO 92
<211> LENGTH: 22
<212> TYPE: DNA
<213> ORGANISM: Artificial
<220> FEATURE:
<223> OTHER INFORMATION: Synthetic

<400> SEQUENCE: 92
tatgtgcctc tactgaccct ac                                                  22

<210> SEQ ID NO 93
<211> LENGTH: 20
<212> TYPE: DNA
<213> ORGANISM: Artificial
<220> FEATURE:
<223> OTHER INFORMATION: Synthetic

<400> SEQUENCE: 93
tgcctctact gaccctactg                                                     20
```

<210> SEQ ID NO 94
<211> LENGTH: 22
<212> TYPE: DNA
<213> ORGANISM: Artificial
<220> FEATURE:
<223> OTHER INFORMATION: Synthetic

<400> SEQUENCE: 94
aagggaaact gggtaagttg tg                                          22

<210> SEQ ID NO 95
<211> LENGTH: 22
<212> TYPE: DNA
<213> ORGANISM: Artificial
<220> FEATURE:
<223> OTHER INFORMATION: Synthetic

<400> SEQUENCE: 95
ctaagggaaa ctgggtaagt tg                                          22

<210> SEQ ID NO 96
<211> LENGTH: 21
<212> TYPE: DNA
<213> ORGANISM: Artificial
<220> FEATURE:
<223> OTHER INFORMATION: Synthetic

<400> SEQUENCE: 96
gacaatatgt gctgccacta c                                           21

<210> SEQ ID NO 97
<211> LENGTH: 19
<212> TYPE: DNA
<213> ORGANISM: Artificial
<220> FEATURE:
<223> OTHER INFORMATION: Synthetic

<400> SEQUENCE: 97
cacagtcccc tccgtctac                                              19

<210> SEQ ID NO 98
<211> LENGTH: 25
<212> TYPE: DNA
<213> ORGANISM: Artificial
<220> FEATURE:
<223> OTHER INFORMATION: Synthetic

<400> SEQUENCE: 98
ggactgcaca tatctgtatt tgtcc                                       25

<210> SEQ ID NO 99
<211> LENGTH: 28
<212> TYPE: DNA
<213> ORGANISM: Artificial
<220> FEATURE:
<223> OTHER INFORMATION: Synthetic

<400> SEQUENCE: 99
ctcactagaa aactttctc taagatcc                                     28

<210> SEQ ID NO 100
<211> LENGTH: 22
<212> TYPE: DNA
<213> ORGANISM: Artificial
<220> FEATURE:
<223> OTHER INFORMATION: Synthetic

```
<400> SEQUENCE: 100
accaggaata caaacatgac tc                                          22

<210> SEQ ID NO 101
<211> LENGTH: 26
<212> TYPE: DNA
<213> ORGANISM: Artificial
<220> FEATURE:
<223> OTHER INFORMATION: Synthetic

<400> SEQUENCE: 101
accaggaata caaacatgac tctttc                                      26

<210> SEQ ID NO 102
<211> LENGTH: 21
<212> TYPE: DNA
<213> ORGANISM: Artificial
<220> FEATURE:
<223> OTHER INFORMATION: Synthetic

<400> SEQUENCE: 102
atagtgggtc ctgcttttca g                                           21

<210> SEQ ID NO 103
<211> LENGTH: 18
<212> TYPE: DNA
<213> ORGANISM: Artificial
<220> FEATURE:
<223> OTHER INFORMATION: Synthetic

<400> SEQUENCE: 103
gtggcaacag gaggcgac                                               18

<210> SEQ ID NO 104
<211> LENGTH: 24
<212> TYPE: DNA
<213> ORGANISM: Artificial
<220> FEATURE:
<223> OTHER INFORMATION: Synthetic

<400> SEQUENCE: 104
ccaccaggaa tacaaacatg actc                                        24

<210> SEQ ID NO 105
<211> LENGTH: 22
<212> TYPE: DNA
<213> ORGANISM: Artificial
<220> FEATURE:
<223> OTHER INFORMATION: Synthetic

<400> SEQUENCE: 105
aaaatatccc ttactgcaaa tg                                          22

<210> SEQ ID NO 106
<211> LENGTH: 20
<212> TYPE: DNA
<213> ORGANISM: Artificial
<220> FEATURE:
<223> OTHER INFORMATION: Synthetic

<400> SEQUENCE: 106
aattgatttc ccaaaaactg                                             20

<210> SEQ ID NO 107
<211> LENGTH: 22
<212> TYPE: DNA
```

```
<213> ORGANISM: Artificial
<220> FEATURE:
<223> OTHER INFORMATION: Synthetic

<400> SEQUENCE: 107
attttacatt gtctgcctgc ac                                        22

<210> SEQ ID NO 108
<211> LENGTH: 21
<212> TYPE: DNA
<213> ORGANISM: Artificial
<220> FEATURE:
<223> OTHER INFORMATION: Synthetic

<400> SEQUENCE: 108
ctgattgtaa atacctatac g                                         21

<210> SEQ ID NO 109
<211> LENGTH: 22
<212> TYPE: DNA
<213> ORGANISM: Artificial
<220> FEATURE:
<223> OTHER INFORMATION: Synthetic

<400> SEQUENCE: 109
gtaccaatat tactatttca gc                                        22

<210> SEQ ID NO 110
<211> LENGTH: 20
<212> TYPE: DNA
<213> ORGANISM: Artificial
<220> FEATURE:
<223> OTHER INFORMATION: Synthetic

<400> SEQUENCE: 110
gtttgtcctt taaatcaacc                                           20

<210> SEQ ID NO 111
<211> LENGTH: 25
<212> TYPE: DNA
<213> ORGANISM: Artificial
<220> FEATURE:
<223> OTHER INFORMATION: Synthetic

<400> SEQUENCE: 111
gtgcatccgt aactacatct tccac                                     25

<210> SEQ ID NO 112
<211> LENGTH: 22
<212> TYPE: DNA
<213> ORGANISM: Artificial
<220> FEATURE:
<223> OTHER INFORMATION: Synthetic

<400> SEQUENCE: 112
atggcctgtg actgcacata cc                                        22

<210> SEQ ID NO 113
<211> LENGTH: 22
<212> TYPE: DNA
<213> ORGANISM: Artificial
<220> FEATURE:
<223> OTHER INFORMATION: Synthetic

<400> SEQUENCE: 113
accatttggg ggaggcgata ac                                        22
```

```
<210> SEQ ID NO 114
<211> LENGTH: 22
<212> TYPE: DNA
<213> ORGANISM: Artificial
<220> FEATURE:
<223> OTHER INFORMATION: Synthetic

<400> SEQUENCE: 114
tgactttgtg tgccactgca ac                                              22

<210> SEQ ID NO 115
<211> LENGTH: 22
<212> TYPE: DNA
<213> ORGANISM: Artificial
<220> FEATURE:
<223> OTHER INFORMATION: Synthetic

<400> SEQUENCE: 115
acatctggtg atacatatac ag                                              22

<210> SEQ ID NO 116
<211> LENGTH: 22
<212> TYPE: DNA
<213> ORGANISM: Artificial
<220> FEATURE:
<223> OTHER INFORMATION: Synthetic

<400> SEQUENCE: 116
ctggcgttgt taccttagcc tg                                              22

<210> SEQ ID NO 117
<211> LENGTH: 22
<212> TYPE: DNA
<213> ORGANISM: Artificial
<220> FEATURE:
<223> OTHER INFORMATION: Synthetic

<400> SEQUENCE: 117
tgtgcctcta ctgaccctac tg                                              22

<210> SEQ ID NO 118
<211> LENGTH: 22
<212> TYPE: DNA
<213> ORGANISM: Artificial
<220> FEATURE:
<223> OTHER INFORMATION: Synthetic

<400> SEQUENCE: 118
ctacacagtc ccctccgtct ac                                              22

<210> SEQ ID NO 119
<211> LENGTH: 24
<212> TYPE: DNA
<213> ORGANISM: Artificial
<220> FEATURE:
<223> OTHER INFORMATION: Synthetic

<400> SEQUENCE: 119
caggaataca aacatgactc tttc                                            24

<210> SEQ ID NO 120
<211> LENGTH: 22
<212> TYPE: DNA
<213> ORGANISM: Artificial
<220> FEATURE:
<223> OTHER INFORMATION: Synthetic
```

<400> SEQUENCE: 120
gctagtggca acaggaggcg ac                                          22

<210> SEQ ID NO 121
<211> LENGTH: 21
<212> TYPE: DNA
<213> ORGANISM: Artificial
<220> FEATURE:
<223> OTHER INFORMATION: Synthetic

<400> SEQUENCE: 121
ccaggaatac aaacatgact c                                           21

<210> SEQ ID NO 122
<211> LENGTH: 22
<212> TYPE: DNA
<213> ORGANISM: Artificial
<220> FEATURE:
<223> OTHER INFORMATION: Synthetic

<400> SEQUENCE: 122
aaggaatacc ttagacatgt gg                                          22

<210> SEQ ID NO 123
<211> LENGTH: 24
<212> TYPE: DNA
<213> ORGANISM: Artificial
<220> FEATURE:
<223> OTHER INFORMATION: Synthetic

<400> SEQUENCE: 123
aaggaatacc ttagacatgt ggaa                                        24

<210> SEQ ID NO 124
<211> LENGTH: 20
<212> TYPE: DNA
<213> ORGANISM: Artificial
<220> FEATURE:
<223> OTHER INFORMATION: Synthetic

<400> SEQUENCE: 124
gcacagggac ataacaatgg                                             20

<210> SEQ ID NO 125
<211> LENGTH: 20
<212> TYPE: DNA
<213> ORGANISM: Artificial
<220> FEATURE:
<223> OTHER INFORMATION: Synthetic

<400> SEQUENCE: 125
gcgcagggcc acaataatgg                                             20

<210> SEQ ID NO 126
<211> LENGTH: 20
<212> TYPE: DNA
<213> ORGANISM: Artificial
<220> FEATURE:
<223> OTHER INFORMATION: Synthetic

<400> SEQUENCE: 126
gcacagggac ataataatgg                                             20

<210> SEQ ID NO 127
<211> LENGTH: 20
<212> TYPE: DNA

<213> ORGANISM: Artificial
<220> FEATURE:
<223> OTHER INFORMATION: Synthetic

<400> SEQUENCE: 127
gcccagggcc acaacaatgg                                          20

<210> SEQ ID NO 128
<211> LENGTH: 20
<212> TYPE: DNA
<213> ORGANISM: Artificial
<220> FEATURE:
<223> OTHER INFORMATION: Synthetic

<400> SEQUENCE: 128
gctcagggtt taaacaatgg                                          20

<210> SEQ ID NO 129
<211> LENGTH: 20
<212> TYPE: DNA
<213> ORGANISM: Artificial
<220> FEATURE:
<223> OTHER INFORMATION: Synthetic

<400> SEQUENCE: 129
cgtcccaaag gaaactgatc                                          20

<210> SEQ ID NO 130
<211> LENGTH: 20
<212> TYPE: DNA
<213> ORGANISM: Artificial
<220> FEATURE:
<223> OTHER INFORMATION: Synthetic

<400> SEQUENCE: 130
cgacctaaag gaaactgatc                                          20

<210> SEQ ID NO 131
<211> LENGTH: 20
<212> TYPE: DNA
<213> ORGANISM: Artificial
<220> FEATURE:
<223> OTHER INFORMATION: Synthetic

<400> SEQUENCE: 131
cgtccaaaag gaaactgatc                                          20

<210> SEQ ID NO 132
<211> LENGTH: 18
<212> TYPE: DNA
<213> ORGANISM: Artificial
<220> FEATURE:
<223> OTHER INFORMATION: Synthetic

<400> SEQUENCE: 132
gccaagggga aactgatc                                            18

<210> SEQ ID NO 133
<211> LENGTH: 20
<212> TYPE: DNA
<213> ORGANISM: Artificial
<220> FEATURE:
<223> OTHER INFORMATION: Synthetic

<400> SEQUENCE: 133
cgtcccaaag gatactgatc                                          20

```
<210> SEQ ID NO 134
<211> LENGTH: 20
<212> TYPE: DNA
<213> ORGANISM: Artificial
<220> FEATURE:
<223> OTHER INFORMATION: Synthetic

<400> SEQUENCE: 134
cgtccaaggg gatactgatc                                              20

<210> SEQ ID NO 135
<211> LENGTH: 20
<212> TYPE: DNA
<213> ORGANISM: Artificial
<220> FEATURE:
<223> OTHER INFORMATION: Synthetic

<400> SEQUENCE: 135
cgacctaaag ggaattgatc                                              20

<210> SEQ ID NO 136
<211> LENGTH: 20
<212> TYPE: DNA
<213> ORGANISM: Artificial
<220> FEATURE:
<223> OTHER INFORMATION: Synthetic

<400> SEQUENCE: 136
cgacctagtg gaaattgatc                                              20

<210> SEQ ID NO 137
<211> LENGTH: 20
<212> TYPE: DNA
<213> ORGANISM: Artificial
<220> FEATURE:
<223> OTHER INFORMATION: Synthetic

<400> SEQUENCE: 137
cgaccaaggg gatattgatc                                              20

<210> SEQ ID NO 138
<211> LENGTH: 18
<212> TYPE: DNA
<213> ORGANISM: Artificial
<220> FEATURE:
<223> OTHER INFORMATION: Synthetic

<400> SEQUENCE: 138
gcccaacgga aactgatc                                                18

<210> SEQ ID NO 139
<211> LENGTH: 20
<212> TYPE: DNA
<213> ORGANISM: Artificial
<220> FEATURE:
<223> OTHER INFORMATION: Synthetic

<400> SEQUENCE: 139
cgacccaagg gaaactggtc                                              20

<210> SEQ ID NO 140
<211> LENGTH: 20
<212> TYPE: DNA
<213> ORGANISM: Artificial
<220> FEATURE:
<223> OTHER INFORMATION: Synthetic
```

```
<400> SEQUENCE: 140
cgtcctaaag gaaactggtc                                            20

<210> SEQ ID NO 141
<211> LENGTH: 20
<212> TYPE: DNA
<213> ORGANISM: Artificial
<220> FEATURE:
<223> OTHER INFORMATION: Synthetic

<400> SEQUENCE: 141
gcgacccaat gcaaattggt                                            20

<210> SEQ ID NO 142
<211> LENGTH: 20
<212> TYPE: DNA
<213> ORGANISM: Artificial
<220> FEATURE:
<223> OTHER INFORMATION: Synthetic

<400> SEQUENCE: 142
cgccctaagg gaaactgggt                                            20

<210> SEQ ID NO 143
<211> LENGTH: 18
<212> TYPE: DNA
<213> ORGANISM: Artificial
<220> FEATURE:
<223> OTHER INFORMATION: Synthetic

<400> SEQUENCE: 143
cgccctaagg gaaactgg                                              18

<210> SEQ ID NO 144
<211> LENGTH: 25
<212> TYPE: DNA
<213> ORGANISM: Artificial
<220> FEATURE:
<223> OTHER INFORMATION: Synthetic

<400> SEQUENCE: 144
gatctagatc tgcagaaaac ttttc                                      25

<210> SEQ ID NO 145
<211> LENGTH: 25
<212> TYPE: DNA
<213> ORGANISM: Artificial
<220> FEATURE:
<223> OTHER INFORMATION: Synthetic

<400> SEQUENCE: 145
gatctagatc tgcagaaaag ctgtc                                      25

<210> SEQ ID NO 146
<211> LENGTH: 25
<212> TYPE: DNA
<213> ORGANISM: Artificial
<220> FEATURE:
<223> OTHER INFORMATION: Synthetic

<400> SEQUENCE: 146
gatctagatc tgcagaaaaa ctgtc                                      25

<210> SEQ ID NO 147
<211> LENGTH: 25
<212> TYPE: DNA
```

```
<213> ORGANISM: Artificial
<220> FEATURE:
<223> OTHER INFORMATION: Synthetic

<400> SEQUENCE: 147
gatctagatc tgcagaaaac ctttc                                          25

<210> SEQ ID NO 148
<211> LENGTH: 24
<212> TYPE: DNA
<213> ORGANISM: Artificial
<220> FEATURE:
<223> OTHER INFORMATION: Synthetic

<400> SEQUENCE: 148
ggacataaca atggtatttg ttgg                                           24

<210> SEQ ID NO 149
<211> LENGTH: 24
<212> TYPE: DNA
<213> ORGANISM: Artificial
<220> FEATURE:
<223> OTHER INFORMATION: Synthetic

<400> SEQUENCE: 149
ggacataaca atggtatttg ctgg                                           24

<210> SEQ ID NO 150
<211> LENGTH: 24
<212> TYPE: DNA
<213> ORGANISM: Artificial
<220> FEATURE:
<223> OTHER INFORMATION: Synthetic

<400> SEQUENCE: 150
ggacataaca atggcatttg ctgg                                           24

<210> SEQ ID NO 151
<211> LENGTH: 24
<212> TYPE: DNA
<213> ORGANISM: Artificial
<220> FEATURE:
<223> OTHER INFORMATION: Synthetic

<400> SEQUENCE: 151
ggacacaaca atggcatatg ctgg                                           24

<210> SEQ ID NO 152
<211> LENGTH: 24
<212> TYPE: DNA
<213> ORGANISM: Artificial
<220> FEATURE:
<223> OTHER INFORMATION: Synthetic

<400> SEQUENCE: 152
ggacataaca atggcatttg ttgg                                           24

<210> SEQ ID NO 153
<211> LENGTH: 24
<212> TYPE: DNA
<213> ORGANISM: Artificial
<220> FEATURE:
<223> OTHER INFORMATION: Synthetic

<400> SEQUENCE: 153
ggtttaaaca atggtatttg ttgg                                           24
```

```
<210> SEQ ID NO 154
<211> LENGTH: 22
<212> TYPE: DNA
<213> ORGANISM: Artificial
<220> FEATURE:
<223> OTHER INFORMATION: Synthetic

<400> SEQUENCE: 154
tctagatcar tttcctttgg ga                                              22
```

HPV PRIMERS

The present application claims priority to U.S. Provisional Application Ser. No. 60/842,301, filed Sep. 5, 2006, which is herein incorporated by reference.

FIELD OF THE INVENTION

The present invention provides methods, kits, and compositions related to human papillomavirus (HPV) primers, which may be used, for example, in nucleic acid detection assays for use in basic research, clinical research, and for the development of clinical detection assays.

BACKGROUND

Cervical cancer accounts for nearly 10% of all female cancers and is a leading cause of cancer among women in developing countries (Franco, E. L. et al., Can Med Assoc J. 2001; 164:1017-25). The regions with the highest incidence of the disease are generally those with the greatest mortality and include Central America, Africa, and the Carribean (Ferlay, J. et al., 1998. IARC CancerBase no. 3. Lyon:IARC-Press.). Incidence in Europe and North America has declined precipitously over the past 50 years, possibly due to the advent of routine screening by Papanicolaou (Pap) smear testing (reviewed in Franco et al., ibid). Cervical cancer is one of the most preventable cancers, with survival being directly related to the stage of the disease at diagnosis. The 5-year survival rate is 88% for women having initial diagnosis of localized disease as opposed to 13% for women diagnosed with distant disease (Report of the Gynecologic Cancers Progress Review Group, November 2001, National Cancer Institute). More than 50% of women diagnosed with cervical cancer in the U.S. have not had a Pap smear in the past three years (Wright, T. C. et al., JAMA. 2000; 283:81-6).

Pap screening remains the predominant mode of detecting cancerous and precancerous cervical lesions; more than 50 million women undergo Pap screening each year in the U.S. (Wright, T. C. et al., JAMA 2002; 287:2120-29). Despite its widespread use, Pap smear testing is only partially effective; some estimates place the sensitivity of conventional Pap smear testing at 50-60% (Lorincz, A. T. and Richart, R. M., (Arch Pathol Lab Med. 2003; 127:959-68; Nanda, K. et al., 2000. Ann Intern Med 132:810.; Fahey M T, et al. Am J Epidemiol. 1995; 141:680-9; Myers E R, McCrory D C, Subramanian S, et al. Obstet Gynecol. 2000; 96:645-52.) or 70-80% (Clavel, C. et al., 2001. Br J Cancer 84:1616). Recent innovations in cytological screening and sampling, such as liquid-based tests, have improved the sensitivity of these methods to 75-95% (Lorincz, A. T. et al. ibid; Nanda, K. et al., ibid.; Hutchinson M L, Zahniser D J, Sherman M E, et al. Cancer. 1999; 87:48-55.). Nonetheless, even these improved methods fail to detect a significant portion of abnormal, and often precancerous, cells. Once identified, patients with atypical squamous cells of undetermined significance (AS-CUS) are subjected to various levels of monitoring and treatment, depending on the particular attendant risk factors and clinical presentation (reviewed in Wright, T. C. et al. JAMA 2002, ibid).

Human Papillomavirus (HPV) has been identified as the primary, and possibly only, cause of cervical cancer (Munoz N, Bosch F X, de Sanjosé S, et al., Int J Cancer 1992; 52:743-9; Bosch F X, Lorincz A, Munoz N, Meijer Shah K V., Clin Pathol 2002; 55:244-65), implicated in as many as 99.7% of all cases (Wallboomers, J. M. et al., 1999. J Pathol 189:12-19). The HPV genome is an 8 kb, circular, double stranded DNA comprising 8 genes, all encoded on the same strand. As many as 200 different HPV types have been identified in humans (Burd, E. M. Clin Microbiol Rev. 2003; 16:1-17); of these approximately 40 types have been found capable of infecting the genital tract (Munoz, N. N Engl J Med 2003; 348:518-27.). Still further classification has resulted in the identification of high- and low-risk viral types for development of cervical cancer. Estimates place the number of high-risk types between 13-19 strains, with two strains, HPV 16 and 18 together accounting for as much as 55-85% of infections, depending on subject age and geographical location (Munoz, N., ibid). The predominant low-risk strains are HPV 6 and 11; these may lead to genital warts (reviewed in Burd, E. M., ibid).

The elucidation of certain high risk HPV strains as the causative agents of cervical cancer, coupled with advances in molecular biological methods, has expanded the spectrum of methods available for both preventing and detecting HPV infection. Vaccines for the most common high-risk HPV strains are currently in clinical trials (Koutsky, L A. et al., 2002. NEJM 347:1645-51). Moreover, some authorities are calling for HPV DNA screening for use in conjunction with, or in some cases, in lieu of, conventional cytological methods (Wright, T. C. and Schiffman, M. N. Engl. J. Med, 2003; 348:489-90). Various alternative DNA-based detection methods have been introduced, including the HYBRID CAPTURE II (HCII) test (Digene, Gaithersburg, Md.), which was been approved by the FDA in March, 1999. The HYBRID CAPTURE method relies on hybridization of target DNA to complementary RNA probes. The resultant RNA-DNA hybrids are recognized by surface-bound antibodies as well as antibodies conjugated to alkaline phosphatase, allowing generation of a chemiluminescent signal in the presence of appropriate substrates (Lorincz, A. T. J Obstet Gynaecol Res. 1996; 22:629-36; also U.S. Pat. No. 4,908,306 and related patents and applications). Further alternative methods include the use of sequence specific probes for use in PCR or sandwich hybridization assays, such as those described in U.S. Pat. No. 6,583,278. Other methods rely on various PCR primers for selective amplification of specific strains, as in U.S. Pat. No. 5,447,839 and related applications. Still other methods rely on in situ hybridization of sequence-specific probes to isolated cervical cells, described in WO 00/24760A1 (e.g. INFORM HPV, Ventana Medical Systems, Inc., Tuscon, Ariz.; Qureshi M N et al., Diagn. Cytopathol. 2003; 29:149-155).

Therefore, there exists a need for a rapid, sensitive, and highly quantitative direct detection assay for detecting HPV infection by high risk strains in cervical samples. Given the current reliance on molecular methods, it is likely that there will be an ongoing and increasing need for rapid, quantitative methods of detecting HPV infection.

SUMMARY OF THE INVENTION

The present invention provides methods, kits, and compositions related to human papillomavirus (HPV) primers, which may be used, for example, in nucleic acid detection assays for use in basic research, clinical research, and for the development of clinical detection assays.

In some embodiments, the present invention provides compositions comprising an isolated nucleic acid sequence, wherein the nucleic acid sequence is 70 (e.g., 60 . . . 50 . . . 40 . . . or 30) bases in length or less, and wherein the nucleic acid sequence comprises a nucleotide sequence selected from the group consisting of: SEQ ID NOs:1-123 and 142-154. In other embodiments, the nucleic acid sequence consists of one of the nucleotide sequences shown in SEQ ID NOs:1-123 and 142-154. In certain embodiments, the nucleic acid sequence is 40 bases in length or less. In further embodiments, the nucleic acid sequence is 30 bases in length or less. In particular embodiments, the present invention includes sequences sharing at least 70% sequence identity (e.g., 75%, 80%, 90%, 95%, 98%, or 99%) with any of the above sequences.

In particular embodiments, the compositions further comprise a second isolated nucleic acid sequence different from the isolated nucleic acid sequence, wherein the second nucleic acid sequence is 70 bases in length or less, and wherein the second nucleic acid sequence comprises one of the nucleotide sequences shown in SEQ ID NOs:1-123 and 142-154. In other embodiments, the compositions further comprise at least 5 . . . 10 . . . 15 . . . 20 . . . 50 . . . 100 . . . or 125 additional isolated nucleic acid sequences, wherein the additional nucleic acid sequences are 70 bases in length or less, and wherein the additional nucleic acid sequence each comprises one of the nucleotide sequences shown in SEQ ID NOs:1-123 and 142-154.

In certain embodiments, the present invention provides kits comprising an isolated nucleic acid sequence, wherein the nucleic acid sequence is 70 bases (or 60 . . . 50 . . . 40 . . . or 30 bases) in length or less, and wherein the nucleic acid sequence comprises a nucleotide sequence selected from the group consisting of: SEQ ID NOs:1-123 and 142-154. In other embodiments, the nucleic acid sequence consists of one of the nucleotide sequences shown in SEQ ID NOs:1-123 and 142-154. In further embodiments, the nucleic acid sequence is 40 bases in length or less. In other embodiments, the nucleic acid sequence is 30 bases in length or less.

In some embodiments, the kits further comprise a second isolated nucleic acid sequence different from the isolated nucleic acid sequence, wherein the second nucleic acid sequence is 60 bases in length or less, and wherein the second nucleic acid sequence comprises one of the nucleotide sequences shown in SEQ ID NOs:1-123 and 142-154. In certain embodiments, the kits further comprise at least 20 . . . 40 . . . 60 . . . 80 . . . 100 . . . or 120 additional isolated nucleic acid sequences, wherein the additional nucleic acid sequences are 60 bases in length or less, and wherein the additional nucleic acid sequence each comprises one of the nucleotide sequences shown in SEQ ID NOs:1-123 and 142-154.

In some embodiments, the present invention provides methods for detecting at least one HPV sequence in a sample, comprising using at least one nucleic acid sequence comprising a nucleotide sequence selected from the group consisting of: SEQ ID NOs:1-123 and 142-154. In certain embodiments, the nucleic acid sequence is 60 bases in length or less. In certain embodiments, the detecting allows typing of the HPC sequence. In particular embodiments, the using comprises sequencing with the nucleic acid sequence. In other embodiments, the using comprises amplifying the HPV sequence with the nucleic acid sequence.

In some embodiments, the detected and/or typed HPV sequences are any of those found below in Table 1 or variants thereof (the sequences of which are herein incorporated by reference in their entireties). It is understood that sequences will diverge over time and that other HPV varieties, now know, or later discovered are readily adaptable to the methods and composition of the present invention, per the description herein.

TABLE 1

| strain | accession |
|---|---|
| 1a | NC_001356 |
| 1a | U06714 |
| 2a | X55964 |
| 3 | NC_001588 |
| 3 | X74462 |
| 4 | NC_001457 |
| 4 | X70827 |
| 5 | M17463 |
| 5 | NC_001531 |
| 5b | D90252 |
| 5b | NC_001444 |
| 6a | L41216 |
| 6a | NC_001668 |
| 6b | NC_001355 |
| 6 | AF092932 |
| 6 | NC_000904 |
| 7 | M12588 |
| 7 | NC_001595 |
| 7 | X74463 |
| 8 | M12737 |
| 8 | NC_001532 |
| 9 | NC_001596 |
| 9 | X74464 |
| 10 | NC_001576 |
| 10 | X74465 |
| 11 | J04351 |
| 11 | M14119 |
| 11 | NC_001525 |
| 12 | NC_001577 |
| 12 | X74466 |
| 13 | NC_001349 |
| 13 | X62843 |
| 14d | NC_001578 |
| 14d | X74467 |
| 15 | NC_001579 |
| 15 | X74468 |
| 16 | AF125673 |
| 16 | AF472508 |
| 16 | AF472509 |
| 16 | K02718 |
| 16 | NC_001526 |
| 16 | U89348 |
| 17 | NC_001580 |
| 17 | X74469 |
| 18 | NC_001357 |
| 18 | X05015 |
| 18 | X05349 |
| 19 | NC_001581 |
| 19 | X74470 |
| 20 | NC_001679 |
| 20 | U31778 |
| 21 | NC_001680 |
| 21 | U31779 |
| 22 | NC_001681 |
| 22 | U31780 |
| 23 | NC_001682 |
| 23 | U31781 |
| 24 | NC_001683 |
| 24 | U31782 |
| 25 | NC_001582 |
| 25 | X74471 |
| 26 | NC_001583 |
| 26 | X74472 |
| 27 | NC_001584 |
| 27 | X74473 |
| 28 | NC_001684 |
| 28 | U31783 |
| 29 | NC_001685 |
| 29 | U31784 |
| 30 | NC_001585 |
| 30 | X74474 |
| 31 | J04353 |
| 31 | NC_001527 |
| 32 | NC_001586 |
| 32 | X74475 |
| 33 | M12732 |
| 33 | NC_001528 |
| 34 | NC_001587 |

TABLE 1-continued

| strain | accession |
|---|---|
| 34 | X74476 |
| 35 | M74117 |
| 35 | NC_001529 |
| 35h | X74477 |
| 36 | NC_001686 |
| 36 | U31785 |
| 37 | NC_001687 |
| 37 | U31786 |
| 38 | NC_001688 |
| 38 | U31787 |
| 39 | M62849 |
| 39 | AF548856 |
| 39 | AF548857 |
| 39 | NC_001535 |
| 40 | NC_001589 |
| 40 | X74478 |
| 41 | NC_001354 |
| 41 | X56147 |
| 42 | NC_001534 |
| 42 | M73236 |
| 43 | U12504 |
| 43 | Y12214 |
| 44 | NC_001689 |
| 44 | U31788 |
| 45 | NC_001590 |
| 45 | X74479 |
| 47 | M32305 |
| 47 | NC_001530 |
| 48 | NC_001690 |
| 48 | U31789 |
| 49 | NC_001591 |
| 49 | X74480 |
| 50 | NC_001691 |
| 50 | U31790 |
| 51 | M62877 |
| 51 | NC_001533 |
| 52 | NC_001592 |
| 52 | X74481 |
| 53 | NC_001593 |
| 53 | X74482 |
| 54 | AF436129 |
| 54 | NC_001676 |
| 54 | U37488 |
| 55 | NC_001692 |
| 55 | U31791 |
| 56 | NC_001594 |
| 56 | X74483 |
| 57 | NC_001353 |
| 57 | X55965 |
| 57b | U37537 |
| 58 | D90400 |
| 58 | NC_001443 |
| 59 | NC_001635 |
| 59 | X77858 |
| 60 | NC_001693 |
| 60 | U31792 |
| 61 | NC_001694 |
| 61 | U31793 |
| 62 | U12499 |
| 63 | NC_001458 |
| 63 | X70828 |
| 64 | U12495 |
| 65 | NC_001459 |
| 65 | X70829 |
| 66 | NC_001695 |
| 66 | U31794 |
| 67 | D21208 |
| 68 | M73258 |
| 68 | Y14591 |
| 69 | AB027020 |
| 69 | NC_002171 |
| 70 | NC_001711 |
| 70 | U21941 |
| 71 | AB040456 |
| 71 | NC_002644 |
| 72 | X94164 |
| 73 | X94165 |
| 74 | AF436130 |

TABLE 1-continued

| strain | accession |
|---|---|
| 74 | NC_004501 |
| 75 | Y15173 |
| 76 | Y15174 |
| 77 | Y15175 |
| 80 | Y15176 |
| 82 | AB027021 |
| 82 | AF293961 |
| 82 | NC_002172 |
| 83 | AF151983 |
| 83 | NC_000856 |
| 84 | AF293960 |
| 84 | NC_002676 |
| 85 | AF131950 |
| 86 | AF349909 |
| 86 | NC_003115 |
| 87 | AJ400628 |
| 87 | NC_002627 |
| 89 | NC_004103 |
| 90 | AY057438 |
| 90 | NC_004104 |
| 91 | AF419318 |
| 91 | AF436128 |
| 91 | NC_004085 |
| 92 | AF531420 |
| 92 | NC_004500 |
| RXRX7 | U85660 |

DEFINITIONS

To facilitate an understanding of the present invention, a number of terms and phrases are defined below:

As used herein, the terms "subject" and "patient" refer to any organisms including plants, microorganisms and animals (e.g., mammals such as dogs, cats, livestock, and humans).

As used herein, the term "INVADER assay reagents" refers to one or more reagents for detecting target sequences, said reagents comprising oligonucleotides capable of forming an invasive cleavage structure in the presence of the target sequence. In some embodiments, the INVADER assay reagents further comprise an agent for detecting the presence of an invasive cleavage structure (e.g., a cleavage agent). In some embodiments, the oligonucleotides comprise first and second oligonucleotides, said first oligonucleotide comprising a 5' portion complementary to a first region of the target nucleic acid and said second oligonucleotide comprising a 3' portion and a 5' portion, said 5' portion complementary to a second region of the target nucleic acid downstream of and contiguous to the first portion. In some embodiments, the 3' portion of the second oligonucleotide comprises a 3' terminal nucleotide not complementary to the target nucleic acid. In preferred embodiments, the 3' portion of the second oligonucleotide consists of a single nucleotide not complementary to the target nucleic acid.

In some embodiments, INVADER assay reagents are configured to detect a target nucleic acid sequence comprising first and second non-contiguous single-stranded regions separated by an intervening region comprising a double-stranded region. In preferred embodiments, the INVADER assay reagents comprise a bridging oligonucleotide capable of binding to said first and second non-contiguous single-stranded regions of a target nucleic acid sequence. In particularly preferred embodiments, either or both of said first or said second oligonucleotides of said INVADER assay reagents are bridging oligonucleotides.

In some embodiments, the INVADER assay reagents further comprise a solid support. For example, in some embodiments, the one or more oligonucleotides of the assay reagents (e.g., first and/or second oligonucleotide, whether bridging or non-bridging) is attached to said solid support. In some embodiments, the INVADER assay reagents further comprise a buffer solution. In some preferred embodiments, the buffer solution comprises a source of divalent cations (e.g., $Mn^{2+}$ and/or $Mg^{2+}$ ions). Individual ingredients (e.g., oligonucleotides, enzymes, buffers, target nucleic acids) that collectively make up INVADER assay reagents are termed "INVADER assay reagent components."

In some embodiments, the INVADER assay reagents further comprise a third oligonucleotide complementary to a third portion of the target nucleic acid upstream of the first portion of the first target nucleic acid. In yet other embodiments, the INVADER assay reagents further comprise a target nucleic acid. In some embodiments, the INVADER assay reagents further comprise a second target nucleic acid. In yet other embodiments, the INVADER assay reagents further comprise a third oligonucleotide comprising a 5' portion complementary to a first region of the second target nucleic acid. In some specific embodiments, the 3' portion of the third oligonucleotide is covalently linked to the second target nucleic acid. In other specific embodiments, the second target nucleic acid further comprises a 5' portion, wherein the 5' portion of the second target nucleic acid is the third oligonucleotide. In still other embodiments, the INVADER assay reagents further comprise an ARRESTOR molecule (e.g., ARRESTOR oligonucleotide).

In some preferred embodiments, the INVADER assay reagents further comprise reagents for detecting a nucleic acid cleavage product. In some embodiments, one or more oligonucleotides in the INVADER assay reagents comprise a label. In some preferred embodiments, said first oligonucleotide comprises a label. In other preferred embodiments, said third oligonucleotide comprises a label. In particularly preferred embodiments, the reagents comprise a first and/or a third oligonucleotide labeled with moieties that produce a fluorescence resonance energy transfer (FRET) effect.

In some embodiments one or more the INVADER assay reagents may be provided in a predispensed format (i.e., premeasured for use in a step of the procedure without re-measurement or re-dispensing). In some embodiments, selected INVADER assay reagent components are mixed and predispensed together. In preferred embodiments, predispensed assay reagent components are predispensed and are provided in a reaction vessel (including but not limited to a reaction tube or a well, as in, e.g., a microtiter plate). In particularly preferred embodiments, predispensed INVADER assay reagent components are dried down (e.g., desiccated or lyophilized) in a reaction vessel.

In some embodiments, the INVADER assay reagents are provided as a kit. As used herein, the term "kit" refers to any delivery system for delivering materials. In the context of reaction assays, such delivery systems include systems that allow for the storage, transport, or delivery of reaction reagents (e.g., oligonucleotides, enzymes, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials. As used herein, the term "fragmented kit" refers to delivery systems comprising two or more separate containers that each contains a subportion of the total kit components. The containers may be delivered to the intended recipient together or separately. For example, a first container may contain an enzyme for use in an assay, while a second container contains oligonucleotides. The term "fragmented kit" is intended to encompass kits containing Analyte specific reagents (ASR's) regulated under section 520(e) of the Federal Food, Drug, and Cosmetic Act, but are not limited thereto. Indeed, any delivery system comprising two or more separate containers that each contains a subportion of the total kit components are included in the term "fragmented kit." In contrast, a "combined kit" refers to a delivery system containing all of the components of a reaction assay in a single container (e.g., in a single box housing each of the desired components). The term "kit" includes both fragmented and combined kits.

In some embodiments, the present invention provides INVADER assay reagent kits comprising one or more of the components necessary for practicing the present invention. For example, the present invention provides kits for storing or delivering the enzymes and/or the reaction components necessary to practice an INVADER assay. The kit may include any and all components necessary or desired for assays including, but not limited to, the reagents themselves, buffers, control reagents (e.g., tissue samples, positive and negative control target oligonucleotides, etc.), solid supports, labels, written and/or pictorial instructions and product information, software (e.g., for collecting and analyzing data), inhibitors, labeling and/or detection reagents, package environmental controls (e.g., ice, desiccants, etc.), and the like. In some embodiments, the kits provide a sub-set of the required components, wherein it is expected that the user will supply the remaining components. In some embodiments, the kits comprise two or more separate containers wherein each container houses a subset of the components to be delivered. For example, a first container (e.g., box) may contain an enzyme (e.g., structure specific cleavage enzyme in a suitable storage buffer and container), while a second box may contain oligonucleotides (e.g., INVADER oligonucleotides, probe oligonucleotides, control target oligonucleotides, etc.).

The term "label" as used herein refers to any atom or molecule that can be used to provide a detectable (preferably quantifiable) effect, and that can be attached to a nucleic acid or protein. Labels include but are not limited to dyes; radiolabels such as $^{32}P$; binding moieties such as biotin; haptens such as digoxygenin; luminogenic, phosphorescent or fluorogenic moieties; mass tags; and fluorescent dyes alone or in combination with moieties that can suppress or shift emission spectra by fluorescence resonance energy transfer (FRET). Labels may provide signals detectable by fluorescence, radioactivity, colorimetry, gravimetry, X-ray diffraction or absorption, magnetism, enzymatic activity, characteristics of mass or behavior affected by mass (e.g., MALDI time-of-flight mass spectrometry), and the like. A label may be a charged moiety (positive or negative charge) or alternatively, may be charge neutral. Labels can include or consist of nucleic acid or protein sequence, so long as the sequence comprising the label is detectable.

As used herein, the term "distinct" in reference to signals refers to signals that can be differentiated one from another, e.g., by spectral properties such as fluorescence emission wavelength, color, absorbance, mass, size, fluorescence polarization properties, charge, etc., or by capability of interaction with another moiety, such as with a chemical reagent, an enzyme, an antibody, etc.

As used herein, the terms "complementary" or "complementarity" are used in reference to polynucleotides (i.e., a sequence of nucleotides such as an oligonucleotide or a target nucleic acid) related by the base-pairing rules. For example, for the sequence "5'-A-G-T-3'," is complementary to the sequence "3'-T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids. Either term may also be used in reference to individual nucleotides, especially within the context of polynucleotides. For example, a particular nucleotide within an oligonucleotide may be noted for its complementarity, or lack thereof, to a nucleotide within another nucleic acid strand, in contrast or comparison to the complementarity between the rest of the oligonucleotide and the nucleic acid strand.

The term "homology" and "homologous" refers to a degree of identity. There may be partial homology or complete homology. A partially homologous sequence is one that is less than 100% identical to another sequence.

As used herein, the term "hybridization" is used in reference to the pairing of complementary nucleic acids. Hybridization and the strength of hybridization (i.e., the strength of the association between the nucleic acids) is influenced by such factors as the degree of complementary between the nucleic acids, stringency of the conditions involved, and the $T_m$ of the formed hybrid. "Hybridization" methods involve the annealing of one nucleic acid to another, complementary nucleic acid, i.e., a nucleic acid having a complementary nucleotide sequence. The ability of two polymers of nucleic acid containing complementary sequences to find each other and anneal through base pairing interaction is a well-recognized phenomenon. The initial observations of the "hybridization" process by Marmur and Lane, Proc. Natl. Acad. Sci. USA 46:453 (1960) and Doty et al., Proc. Natl. Acad. Sci. USA 46:461 (1960) have been followed by the refinement of this process into an essential tool of modern biology.

The complement of a nucleic acid sequence as used herein refers to an oligonucleotide which, when aligned with the nucleic acid sequence such that the 5' end of one sequence is paired with the 3' end of the other, is in "antiparallel association." Certain bases not commonly found in natural nucleic acids may be included in the nucleic acids of the present invention and include, for example, inosine and 7-deazaguanine. Complementarity need not be perfect; stable duplexes may contain mismatched base pairs or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs.

As used herein, the term "$T_m$" is used in reference to the "melting temperature." The melting temperature is the temperature at which a population of double-stranded nucleic acid molecules becomes half dissociated into single strands. Several equations for calculating the $T_m$ of nucleic acids are well known in the art. As indicated by standard references, a simple estimate of the $T_m$ value may be calculated by the equation: $T_m=81.5+0.41$ (% G+C), when a nucleic acid is in aqueous solution at 1 M NaCl (see e.g., Anderson and Young, Quantitative Filter Hybridization, in Nucleic Acid Hybridization (1985). Other references (e.g., Allawi, H. T. & SantaLucia, J., Jr. Thermodynamics and NMR of internal G.T mismatches in DNA. Biochemistry 36, 10581-94 (1997) include more sophisticated computations which take structural and environmental, as well as sequence characteristics into account for the calculation of $T_m$.

The term "gene" refers to a DNA sequence that comprises control and coding sequences necessary for the production of an RNA having a non-coding function (e.g., a ribosomal or transfer RNA), a polypeptide or a precursor. The RNA or polypeptide can be encoded by a full length coding sequence or by any portion of the coding sequence so long as the desired activity or function is retained.

The term "wild-type" refers to a gene or a gene product that has the characteristics of that gene or gene product when isolated from a naturally occurring source. A wild-type gene is that which is most frequently observed in a population and is thus arbitrarily designated the "normal" or "wild-type" form of the gene. In contrast, the term "modified", "mutant" or "polymorphic" refers to a gene or gene product which displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

The term "recombinant DNA vector" as used herein refers to DNA sequences containing a desired heterologous sequence. For example, although the term is not limited to the use of expressed sequences or sequences that encode an expression product, in some embodiments, the heterologous sequence is a coding sequence and appropriate DNA sequences necessary for either the replication of the coding sequence in a host organism, or the expression of the operably linked coding sequence in a particular host organism. DNA sequences necessary for expression in prokaryotes include a promoter, optionally an operator sequence, a ribosome binding site and possibly other sequences. Eukaryotic cells are known to utilize promoters, polyadenlyation signals and enhancers.

The term "oligonucleotide" as used herein is defined as a molecule comprising two or more deoxyribonucleotides or ribonucleotides, preferably at least 5 nucleotides, more preferably at least about 10-15 nucleotides and more preferably at least about 15 to 30 nucleotides or more. The exact size will depend on many factors, which in turn depend on the ultimate function or use of the oligonucleotide. The oligonucleotide may be generated in any manner, including chemical synthesis, DNA replication, reverse transcription, PCR, or a combination thereof. In some embodiments, oligonucleotides that form invasive cleavage structures are generated in a reaction (e.g., by extension of a primer in an enzymatic extension reaction).

Because mononucleotides are reacted to make oligonucleotides in a manner such that the 5' phosphate of one mononucleotide pentose ring is attached to the 3' oxygen of its neighbor in one direction via a phosphodiester linkage, an end of an oligonucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may be said to have 5' and 3' ends. A first region along a nucleic acid strand is said to be upstream of another region if the 3' end of the first region is before the 5' end of the second region when moving along a strand of nucleic acid in a 5' to 3' direction.

When two different, non-overlapping oligonucleotides anneal to different regions of the same linear complementary nucleic acid sequence, and the 3' end of one oligonucleotide points towards the 5' end of the other, the former may be called the "upstream" oligonucleotide and the latter the "downstream" oligonucleotide. Similarly, when two overlapping oligonucleotides are hybridized to the same linear complementary nucleic acid sequence, with the first oligonucleotide positioned such that its 5' end is upstream of the 5' end of the second oligonucleotide, and the 3' end of the first oligonucleotide is upstream of the 3' end of the second oligonucleotide, the first oligonucleotide may be called the "upstream" oligonucleotide and the second oligonucleotide may be called the "downstream" oligonucleotide.

The term "primer" refers to an oligonucleotide that is capable of acting as a point of initiation of synthesis when placed under conditions in which primer extension is initiated. An oligonucleotide "primer" may occur naturally, as in a purified restriction digest or may be produced synthetically.

A primer is selected to be "substantially" complementary to a strand of specific sequence of the template. A primer must be sufficiently complementary to hybridize with a template strand for primer elongation to occur. A primer sequence need not reflect the exact sequence of the template. For example, a non-complementary nucleotide fragment may be attached to the 5' end of the primer, with the remainder of the primer sequence being substantially complementary to the strand. Non-complementary bases or longer sequences can be interspersed into the primer, provided that the primer sequence has sufficient complementarity with the sequence of the template to hybridize and thereby form a template primer complex for synthesis of the extension product of the primer.

The term "cleavage structure" as used herein, refers to a structure that is formed by the interaction of at least one probe oligonucleotide and a target nucleic acid, forming a structure comprising a duplex, the resulting structure being cleavable by a cleavage means, including but not limited to an enzyme. The cleavage structure is a substrate for specific cleavage by the cleavage means in contrast to a nucleic acid molecule that is a substrate for non-specific cleavage by agents such as phosphodiesterases which cleave nucleic acid molecules without regard to secondary structure (i.e., no formation of a duplexed structure is required).

The term "cleavage means" or "cleavage agent" as used herein refers to any means that is capable of cleaving a cleavage structure, including but not limited to enzymes. "Structure-specific nucleases" or "structure-specific enzymes" are enzymes that recognize specific secondary structures in a nucleic molecule and cleave these structures. The cleavage means of the invention cleave a nucleic acid molecule in response to the formation of cleavage structures; it is not necessary that the cleavage means cleave the cleavage structure at any particular location within the cleavage structure.

The cleavage means may include nuclease activity provided from a variety of sources including the Cleavase enzymes, the FEN-1 endonucleases (including RAD2 and XPG proteins), Taq DNA polymerase and E. coli DNA polymerase I. The cleavage means may include enzymes having 5' nuclease activity (e.g., Taq DNA polymerase (DNAP), E. coli DNA polymerase I). The cleavage means may also include modified DNA polymerases having 5' nuclease activity but lacking synthetic activity. Examples of cleavage means suitable for use in the method and kits of the present invention are provided in U.S. Pat. Nos. 5,614,402; 5,795,763; 5,843,669; 6,090; PCT Appln. Nos WO 98/23774; WO 02/070755A2; and WO0190337A2, each of which is herein incorporated by reference it its entirety.

The term "thermostable" when used in reference to an enzyme, such as a 5' nuclease, indicates that the enzyme is functional or active (i.e., can perform catalysis) at an elevated temperature, i.e., at about 55° C. or higher.

The term "cleavage products" as used herein, refers to products generated by the reaction of a cleavage means with a cleavage structure (i.e., the treatment of a cleavage structure with a cleavage means).

The term "target nucleic acid" refers to a nucleic acid molecule containing a sequence that has at least partial complementarity with at least a probe oligonucleotide and may also have at least partial complementarity with an INVADER oligonucleotide. The target nucleic acid may comprise single- or double-stranded DNA or RNA.

The term "non-target cleavage product" refers to a product of a cleavage reaction that is not derived from the target nucleic acid. As discussed above, in the methods of the present invention, cleavage of the cleavage structure generally occurs within the probe oligonucleotide. The fragments of the probe oligonucleotide generated by this target nucleic acid-dependent cleavage are "non-target cleavage products."

The term "probe oligonucleotide" refers to an oligonucleotide that interacts with a target nucleic acid to form a cleavage structure in the presence or absence of an INVADER oligonucleotide. When annealed to the target nucleic acid, the probe oligonucleotide and target form a cleavage structure and cleavage occurs within the probe oligonucleotide.

The term "INVADER oligonucleotide" refers to an oligonucleotide that hybridizes to a target nucleic acid at a location near the region of hybridization between a probe and the target nucleic acid, wherein the INVADER oligonucleotide comprises a portion (e.g., a chemical moiety, or nucleotide-whether complementary to that target or not) that overlaps with the region of hybridization between the probe and target. In some embodiments, the INVADER oligonucleotide contains sequences at its 3' end that are substantially the same as sequences located at the 5' end of a probe oligonucleotide.

The term "cassette" as used herein refers to an oligonucleotide or combination of oligonucleotides configured to generate a detectable signal in response to cleavage of a probe oligonucleotide in an INVADER assay. In preferred embodiments, the cassette hybridizes to a non-target cleavage product from cleavage of the probe oligonucleotide to form a second invasive cleavage structure, such that the cassette can then be cleaved.

In some embodiments, the cassette is a single oligonucleotide comprising a hairpin portion (i.e., a region wherein one portion of the cassette oligonucleotide hybridizes to a second portion of the same oligonucleotide under reaction conditions, to form a duplex). In other embodiments, a cassette comprises at least two oligonucleotides comprising complementary portions that can form a duplex under reaction conditions. In preferred embodiments, the cassette comprises a label. In particularly preferred embodiments, cassette comprises labeled moieties that produce a fluorescence resonance energy transfer (FRET) effect.

The term "substantially single-stranded" when used in reference to a nucleic acid substrate means that the substrate molecule exists primarily as a single strand of nucleic acid in contrast to a double-stranded substrate which exists as two strands of nucleic acid which are held together by inter-strand base pairing interactions.

As used herein, the phrase "non-amplified oligonucleotide detection assay" refers to a detection assay configured to detect the presence or absence of a particular polymorphism (e.g., SNP, repeat sequence, etc.) in a target sequence (e.g. genomic DNA) that has not been amplified (e.g. by PCR), without creating copies of the target sequence. A "non-amplified oligonucleotide detection assay" may, for example, amplify a signal used to indicate the presence or absence of a particular polymorphism in a target sequence, so long as the target sequence is not copied.

The term "sequence variation" as used herein refers to differences in nucleic acid sequence between two nucleic acids. For example, a wild-type structural gene and a mutant form of this wild-type structural gene may vary in sequence by the presence of single base substitutions and/or deletions or insertions of one or more nucleotides. These two forms of the structural gene are said to vary in sequence from one another. A second mutant form of the structural gene may exist. This second mutant form is said to vary in sequence from both the wild-type gene and the first mutant form of the gene.

The term "liberating" as used herein refers to the release of a nucleic acid fragment from a larger nucleic acid fragment, such as an oligonucleotide, by the action of, for example, a 5' nuclease such that the released fragment is no longer covalently attached to the remainder of the oligonucleotide.

The term "$K_m$" as used herein refers to the Michaelis-Menten constant for an enzyme and is defined as the concentration of the specific substrate at which a given enzyme yields one-half its maximum velocity in an enzyme catalyzed reaction.

The term "nucleotide analog" as used herein refers to modified or non-naturally occurring nucleotides including but not limited to analogs that have altered stacking interactions such as 7-deaza purines (i.e., 7-deaza-dATP and 7-deaza-dGTP); base analogs with alternative hydrogen bonding configurations (e.g., such as Iso-C and Iso-G and other non-standard base pairs described in U.S. Pat. No. 6,001,983 to S. Benner); non-hydrogen bonding analogs (e.g., non-polar, aromatic nucleoside analogs such as 2,4-difluorotoluene, described by B. A. Schweitzer and E. T. Kool, J. Org. Chem., 1994, 59, 7238-7242, B. A. Schweitzer and E. T. Kool, J. Am. Chem. Soc., 1995, 117, 1863-1872); "universal" bases such as 5-nitroindole and 3-nitropyrrole; and universal purines and pyrimidines (such as "K" and "P" nucleotides, respectively; P. Kong, et al., Nucleic Acids Res., 1989, 17, 10373-10383, P. Kong et al., Nucleic Acids Res., 1992, 20, 5149-5152). Nucleotide analogs include comprise modified forms of deoxyribonucleotides as well as ribonucleotides.

The term "polymorphic locus" is a locus present in a population that shows variation between members of the population (e.g., the most common allele has a frequency of less than 0.95). In contrast, a "monomorphic locus" is a genetic locus at little or no variations seen between members of the population (generally taken to be a locus at which the most common allele exceeds a frequency of 0.95 in the gene pool of the population).

The term "microorganism" as used herein means an organism too small to be observed with the unaided eye and includes, but is not limited to bacteria, virus, protozoans, fungi, and ciliates.

The term "microbial gene sequences" refers to gene sequences derived from a microorganism.

The term "bacteria" refers to any bacterial species including eubacterial and archaebacterial species.

As used herein, the terms "high-risk HPV strains" or "high-risk HPV types" refer to those strains of HPV that have been found in cancers (e.g., carcinomas). These HPV strains include HPV types 16, 18, 30, 31, 33, 35, 39, 45, 51, 52, 56, 58, 59, 67, 68, 69 and 70.

The term "virus" refers to obligate, ultramicroscopic, intracellular parasites incapable of autonomous replication (i.e., replication requires the use of the host cell's machinery).

The term "multi-drug resistant" or "multiple-drug resistant" refers to a microorganism that is resistant to more than one of the antibiotics or antimicrobial agents used in the treatment of said microorganism.

The term "sample" in the present specification and claims is used in its broadest sense. On the one hand it is meant to include a specimen or culture (e.g., microbiological cultures). On the other hand, it is meant to include both biological and environmental samples. A sample may include a specimen of synthetic origin.

Biological samples may be animal, including human, fluid, solid (e.g., stool) or tissue, as well as liquid and solid food and feed products and ingredients such as dairy items, vegetables, meat and meat by-products, and waste. Biological samples may be obtained from all of the various families of domestic animals, as well as feral or wild animals, including, but not limited to, such animals as ungulates, bear, fish, lagamorphs, rodents, etc.

Environmental samples include environmental material such as surface matter, soil, water and industrial samples, as well as samples obtained from food and dairy processing instruments, apparatus, equipment, utensils, disposable and non-disposable items. These examples are not to be construed as limiting the sample types applicable to the present invention.

The term "source of target nucleic acid" refers to any sample that contains nucleic acids (RNA or DNA). Particularly preferred sources of target nucleic acids are biological samples including, but not limited to blood, saliva, cerebral spinal fluid, pleural fluid, milk, lymph, sputum and semen.

An oligonucleotide is said to be present in "excess" relative to another oligonucleotide (or target nucleic acid sequence) if that oligonucleotide is present at a higher molar concentration that the other oligonucleotide (or target nucleic acid sequence). When an oligonucleotide such as a probe oligonucleotide is present in a cleavage reaction in excess relative to the concentration of the complementary target nucleic acid sequence, the reaction may be used to indicate the amount of the target nucleic acid present. Typically, when present in excess, the probe oligonucleotide will be present at least a 100-fold molar excess; typically at least 1 pmole of each probe oligonucleotide would be used when the target nucleic acid sequence was present at about 10 fmoles or less.

A sample "suspected of containing" a first and a second target nucleic acid may contain either, both or neither target nucleic acid molecule.

The term "reactant" is used herein in its broadest sense. The reactant can comprise, for example, an enzymatic reactant, a chemical reactant or light (e.g., ultraviolet light, particularly short wavelength ultraviolet light is known to break oligonucleotide chains). Any agent capable of reacting with an oligonucleotide to either shorten (i.e., cleave) or elongate the oligonucleotide is encompassed within the term "reactant."

As used herein, the term "purified" or "to purify" refers to the removal of contaminants from a sample. For example, recombinant CLEAVASE nucleases are expressed in bacterial host cells and the nucleases are purified by the removal of host cell proteins; the percent of these recombinant nucleases is thereby increased in the sample.

As used herein the term "portion" when in reference to a protein (as in "a portion of a given protein") refers to fragments of that protein. The fragments may range in size from four amino acid residues to the entire amino acid sequence minus one amino acid (e.g., 4, 5, 6, . . . , n–1).

The term "nucleic acid sequence" as used herein refers to an oligonucleotide, nucleotide or polynucleotide, and fragments or portions thereof, and to DNA or RNA of genomic or synthetic origin that may be single or double stranded, and represent the sense or antisense strand. Similarly, "amino acid sequence" as used herein refers to peptide or protein sequence.

As used herein, the terms "purified" or "substantially purified" refer to molecules, either nucleic or amino acid sequences, that are removed from their natural environment, isolated or separated, and are at least 60% free, preferably 75% free, and most preferably 90% free from other components with which they are naturally associated. An "isolated polynucleotide" or "isolated oligonucleotide" is therefore a substantially purified polynucleotide.

The term "continuous strand of nucleic acid" as used herein is means a strand of nucleic acid that has a continuous, covalently linked, backbone structure, without nicks or other disruptions. The disposition of the base portion of each nucleotide, whether base-paired, single-stranded or mismatched, is not an element in the definition of a continuous strand. The backbone of the continuous strand is not limited to the ribose-phosphate or deoxyribose-phosphate compositions that are found in naturally occurring, unmodified nucleic acids. A nucleic acid of the present invention may comprise modifications in the structure of the backbone, including but not limited to phosphorothioate residues, phosphonate residues, 2' substituted ribose residues (e.g., 2'-O-methyl ribose) and alternative sugar (e.g., arabinose) containing residues.

The term "continuous duplex" as used herein refers to a region of double stranded nucleic acid in which there is no disruption in the progression of basepairs within the duplex (i.e., the base pairs along the duplex are not distorted to accommodate a gap, bulge or mismatch with the confines of the region of continuous duplex). As used herein the term refers only to the arrangement of the basepairs within the duplex, without implication of continuity in the backbone portion of the nucleic acid strand. Duplex nucleic acids with uninterrupted basepairing, but with nicks in one or both strands are within the definition of a continuous duplex.

The term "duplex" refers to the state of nucleic acids in which the base portions of the nucleotides on one strand are bound through hydrogen bonding the their complementary bases arrayed on a second strand. The condition of being in a duplex form reflects on the state of the bases of a nucleic acid. By virtue of base pairing, the strands of nucleic acid also generally assume the tertiary structure of a double helix, having a major and a minor groove. The assumption of the helical form is implicit in the act of becoming duplexed.

The term "template" refers to a strand of nucleic acid on which a complementary copy is built from nucleoside triphosphates through the activity of a template-dependent nucleic acid polymerase. Within a duplex the template strand is, by convention, depicted and described as the "bottom" strand. Similarly, the non-template strand is often depicted and described as the "top" strand.

DESCRIPTION OF THE INVENTION

The present invention provides methods, kits, and compositions related to human papillomavirus (HPV) primers, which may be used, for example, in nucleic acid detection assays for use in basic research, clinical research, and for the development of clinical detection assays. Exemplary primers include SEQ ID NOs:1-123 and 142-154 as shown in Tables 2-5 below.

TABLE 2

| Strain | Primer type | SEQ ID NO: | Sequence | Location |
|---|---|---|---|---|
| 59 | forward | SEQ ID NO: 1 | TCGCAGCACCAATCTTtctg | 86 -> 105 |
| 59 | forward | SEQ ID NO: 2 | CACCAATCTTTCTGTGtgtg | 92 -> 111 |
| 59 | reverse | SEQ ID NO: 3 | GTTTAACTGGCGGTGCggtg | 372 -> 391 |
| 59 | reverse | SEQ ID NO: 4 | GTTACAGCAGCAGATTgaac | 340 -> 359 |
| 16 | forward | SEQ ID NO: 5 | ATAACCTTAACTGCAGacg | 216 -> 234 |
| 16 | forward | SEQ ID NO: 6 | GAGGCACACTAGAAGatac | 287 -> 305 |
| 16 | forward | SEQ ID NO: 7 | GAATATGATTTACAGTTTATTTTTCAACT | 178 -> 207 |
| 16 | forward | SEQ ID NO: 8 | TGTGCTGCCATATCTActtc | 108 -> 127 |
| 16 | reverse | SEQ ID NO: 9 | CCTATAAGTATCTTCTAGtgtg | 311 -> 332 |
| 16 | reverse | SEQ ID NO: 10 | ATCTTCTAGTGTGCCTcctg | 304 -> 323 |
| 18 | forward | SEQ ID NO: 11 | ATATGTGCTTCTACACAGtctc | 105 -> 126 |
| 18 | forward | SEQ ID NO: 12 | CCAATTTAACAATATGTGCttc | 94 -> 115 |
| 18 | reverse | SEQ ID NO: 13 | ATCCACCAAACTAGTAgttg | 307 -> 326 |
| 18 | reverse | SEQ ID NO: 14 | TTGACAGGTAATAGCAacag | 346 -> 365 |
| 31 | forward | SEQ ID NO: 15 | CAATTGCAAACAGTGatac | 115 -> 133 |
| 31 | forward | SEQ ID NO: 16 | AGAGTATTTAAGACATGGtgag | 158 -> 179 |
| 31 | reverse | SEQ ID NO: 17 | GTGTGGTCAATCCAAAAttcc | 280 -> 300 |
| 31 | reverse | SEQ ID NO: 18 | GAGGGAGGTGTGGTCAatcc | 288 -> 307 |
| 31 | reverse | SEQ ID NO: 19 | GGAGGTGTGGTCAAtcc | 288 -> 307 |
| 33 | forward | SEQ ID NO: 20 | CTAATATGACTTTATGCacac | 94 -> 114 |
| 33 | forward | SEQ ID NO: 21 | ATATGACTTTATGCACAcaag | 97 -> 117 |
| 33 | reverse | SEQ ID NO: 22 | TATAGGTATCCTGTAAACtagc | 306 -> 327 |
| 33 | reverse | SEQ ID NO: 23 | GACACGTAATAGCCTGagag | 338 -> 357 |
| 33 | reverse | SEQ ID NO: 24 | TATAGGTATCCTGTAAACTAgca | 306 -> 327 |
| 35 | forward | SEQ ID NO: 25 | GTCTGTGTGTTCTGCTGtgtc | 101 -> 121 |
| 35 | forward | SEQ ID NO: 26 | TTAAGGAATATTTAAGGCatgg | 159 -> 180 |
| 35 | reverse | SEQ ID NO: 27 | GGATCATCTTTAGGTTttgg | 375 -> 394 |
| 35 | reverse | SEQ ID NO: 28 | CTGGGTTTTTGACAAGTTacag | 349 -> 370 |
| 39 | forward | SEQ ID NO: 29 | TATAGAGTCTTCCATACcttc | 116 -> 136 |
| 39 | forward | SEQ ID NO: 30 | ACCAACTTTACATTATCtacc | 93 -> 113 |
| 39 | reverse | SEQ ID NO: 31 | CAGATGGTGGAGGAGCTacag | 292 -> 312 |
| 39 | reverse | SEQ ID NO: 32 | AACATTCCAAAACTTTAgacc | 405 -> 425 |
| 45 | forward | SEQ ID NO: 33 | AATTTAACATTATGTGcctc | 96 -> 115 |
| 45 | forward | SEQ ID NO: 34 | CTAATTTAACATTATGTGcctc | 94 -> 115 |

TABLE 2-continued

| Strain | Primer type | SEQ ID NO: | Sequence | Location |
|---|---|---|---|---|
| 45 | reverse | SEQ ID NO: 35 | GGTAACAGCAACTGATTgcac | 339 -> 359 |
| 45 | reverse | SEQ ID NO: 36 | AACTTGTAGTAGGTGGTggag | 298 -> 318 |
| 51 | forward | SEQ ID NO: 37 | TTTACTCCAAGTAACTTTaagc | 138 -> 159 |
| 51 | forward | SEQ ID NO: 38 | AATCAGCTTTTTATTAcctg | 54 -> 73 |
| 51 | forward | SEQ ID NO: 39 | CTCCAAGTAACTTTAAGCAATat | 142 -> 165 |
| 51 | reverse | SEQ ID NO: 40 | CATCCTCCAAACTAGCagac | 305 -> 324 |
| 51 | reverse | SEQ ID NO: 41 | CGTTCCTTTAAATCAACatcc | 416 -> 436 |
| 51 | reverse | SEQ ID NO: 42 | ACATCCCAAAATTTATATTTgg | 399 -> 420 |
| 52 | forward | SEQ ID NO: 43 | AATTTTAAGGAATACCttcg | 147 -> 166 |
| 52 | forward | SEQ ID NO: 44 | AATTTTAAGGAATACCTTcgtc | 147 -> 168 |
| 52 | forward | SEQ ID NO: 45 | CATGACTTTATGTGctga | 98 -> 115 |
| 52 | forward | SEQ ID NO: 46 | AACATGACTTTATGTGCtga | 96 -> 115 |
| 52 | forward | SEQ ID NO: 47 | GAAAATTTTAAGGAATACCTtcg | 145 -> 166 |
| 52 | reverse | SEQ ID NO: 48 | CCAAGATGCAGACGGTggtg | 295 -> 315 |
| 52 | reverse | SEQ ID NO: 49 | AATCTGTATGTGTCCTCCaaag | 310 -> 331 |
| 56 | forward | SEQ ID NO: 50 | ATGCACGAAAAATTAAtcag | 139 -> 158 |
| 56 | forward | SEQ ID NO: 51 | CAGTTAAGTAAATATGATgcac | 123 -> 144 |
| 56 | reverse | SEQ ID NO: 52 | GTCCTGTTTTTCTGTTggtg | 370 -> 389 |
| 56 | reverse | SEQ ID NO: 53 | TCTATATTTATCTTCTaggc | 310 -> 329 |
| 58 | forward | SEQ ID NO: 54 | CTAATATGACATTATGCactg | 94 -> 114 |
| 58 | forward | SEQ ID NO: 55 | ACAGTTTGTTTTTCAGCTttgc | 188 -> 209 |
| 58 | reverse | SEQ ID NO: 56 | TTGGCAAGTAATAGCCTGggag | 338 -> 359 |
| 58 | reverse | SEQ ID NO: 57 | CTGGGAGGTAACAaatc | 328 -> 344 |
| 58 | reverse | SEQ ID NO: 58 | GAGGTAACAAATCTATATGTGtc | 318 -> 340 |
| 58 | reverse | SEQ ID NO: 59 | TGCTGTTTTTTGGCaag | 350 -> 371 |
| 66 | forward | SEQ ID NO: 60 | GCAGCTAAAAGCACATtaac | 111 -> 130 |
| 66 | forward | SEQ ID NO: 61 | CGTGAAATCAATCAATACcttc | 144 -> 165 |
| 66 | reverse | SEQ ID NO: 62 | TCCCAAAACTTATATTTagcc | 395 -> 415 |
| 66 | reverse | SEQ ID NO: 63 | TACCTATATTTATCCTCTaagc | 310 -> 331 |
| 68 | forward | SEQ ID NO: 64 | AATATGTTAGGCATGTtgag | 163 -> 182 |
| 68 | forward | SEQ ID NO: 65 | GGAATATGTTAGGCATGTtgag | 164 -> 182 |
| 68 | reverse | SEQ ID NO: 66 | ATCTACAAGACTAGCAGatgg | 306 -> 326 |
| 68 | reverse | SEQ ID NO: 67 | TATGTATCTACAAGACtagc | 312 -> 331 |
| 52 | forward | SEQ ID NO: 68 | ACTAACATGACTTTATGTgctg | 93 -> 114 |
| 52 | forward | SEQ ID NO: 69 | CACTAACATGACTTTATGTGctga | 92 -> 115 |
| 16 | forward | SEQ ID NO: 70 | CGCAGTACAAATAtgtc | 77 -> 93 |
| 16 | forward | SEQ ID NO: 71 | gctgccatatctacttcag | 111 -> 129 |
| 16 | forward | SEQ ID NO: 72 | agtacctacgacatggg | 160 -> 176 |
| 35 | forward | SEQ ID NO: 73 | ATTTTAAGGAATATTTAAGGCatgg | 159 -> 180 |
| 35 | forward | SEQ ID NO: 74 | GAATATTTAAGGCATGGTgaag | 159 -> 180 |
| 68 | forward | SEQ ID NO: 75 | ATATGTTAGGCATGTtgag | 164 -> 182 |
| 18 | forward | SEQ ID NO: 76 | GTGCTTCTACACAGTct | 104 -> 125 |
| 18 | forward | SEQ ID NO: 77 | AATATGTGCTTCTACACagtc | 104 -> 124 |

TABLE 3

| Strain | Primer type | SEQ ID NO: | Sequence | Location |
|---|---|---|---|---|
| 06 | forward | SEQ ID NO: 78 | GCATCCGTAACTACATCTTccac | 109 -> 133 |
| 06 | forward | SEQ ID NO: 79 | CGTAACTACATCTTCCACATacac | 116 -> 139 |
| 06 | reverse | SEQ ID NO: 80 | GCCTGTGACTGCACAtacc | 331 -> 352 |
| 06 | reverse | SEQ ID NO: 81 | CATTTGGGGAGGCGAtaac | 290 -> 311 |
| 11 | forward | SEQ ID NO: 82 | ACACGCAGTACAAATATGacac | 84 -> 105 |
| 11 | forward | SEQ ID NO: 83 | TGTGCATCTGTGTCTAAAtctg | 108 -> 129 |
| 11 | reverse | SEQ ID NO: 84 | CATTTGGTGGAGGCGATAaacc | 285 -> 306 |
| 11 | reverse | SEQ ID NO: 85 | ACCTCCCAAAAACTCATatcc | 398 -> 418 |
| 26 | forward | SEQ ID NO: 86 | CTTACCATTAGTACATTATctg | 99 -> 120 |
| 26 | reverse | SEQ ID NO: 87 | GACAGGTAGTAGCAgag | 347 -> 368 |
| 42 | forward | SEQ ID NO: 88 | CTTTGTGTGCCACTGcaac | 100 -> 121 |
| 42 | forward | SEQ ID NO: 89 | GCAACATCTGGTGATACATATacag | 120 -> 141 |
| 42 | reverse | SEQ ID NO: 90 | GGCGTTGTTACCTTAGcctg | 357 -> 378 |

TABLE 3-continued

| Strain | Primer type | SEQ ID NO: | Sequence | Location |
|---|---|---|---|---|
| 42 | reverse | SEQ ID NO: 91 | ACCTCCCAAAACCAAAAGtctg | 397 -> 418 |
| 43 | forward | SEQ ID NO: 92 | TATGTGCCTCTACTGACCctac | 06 -> 127 |
| 43 | forward | SEQ ID NO: 93 | TGCCTCTACTGACCCTactg | 108 -> 129 |
| 43 | reverse | SEQ ID NO: 94 | AAGGGAAACTGGGTAAGTtgtg | 448 -> 469 |
| 43 | reverse | SEQ ID NO: 95 | CTAAGGGAAACTGGGTAAgttg | 450 -> 471 |
| 44 | forward | SEQ ID NO: 96 | GACAATATGTGCTGCCActac | 121 -> 141 |
| 44 | forward | SEQ ID NO: 97 | CACAGTCCCCTCCGTctac | 138 -> 159 |
| 44 | reverse | SEQ ID NO: 98 | GGACTGCACATATCTGTATTTgtcc | 323 -> 348 |
| 44 | reverse | SEQ ID NO: 99 | CTCACTAGAAAACTTTTCTCTAAGatcc | 425 -> 452 |
| 53 | forward | SEQ ID NO: 100 | ACCAGGAATACAAACATGactc | 84 -> 105 |
| 53 | forward | SEQ ID NO: 101 | ACCAGGAATACAAACATGACTCtttc | 87 -> 109 |
| 53 | reverse | SEQ ID NO: 102 | ATAGTGGGTCCTGCTTTTcag | 376 -> 396 |
| 53 | reverse | SEQ ID NO: 103 | GTGGCAACAGGAGGcgac | 290 -> 311 |
| 53 | forward | SEQ ID NO: 104 | CCACCAGGAATACAAACATGactc | 85 -> 105 |
| 67 | forward | SEQ ID NO: 105 | AAAATATCCCTTACTGCAAatg | 210 -> 231 |
| 67 | reverse | SEQ ID NO: 106 | AATTGATTTCCCAAAAActg | 404 -> 423 |
| 70 | forward | SEQ ID NO: 107 | ATTTTACATTGTCTGCCTGcac | 97 -> 118 |
| 70 | reverse | SEQ ID NO: 108 | CTGATTGTAAATACCTATacg | 328 -> 348 |
| 83 | forward | SEQ ID NO: 109 | GTACCAATATTACTATTTCagc | 91 -> 112 |
| 83 | reverse | SEQ ID NO: 110 | GTTTGTCCTTTAAATCAacc | 421 -> 440 |
| 06 | forward | SEQ ID NO: 111 | GTGCATCCGTAACTACATCTTccac | 109 -> 133 |
| 06 | reverse | SEQ ID NO: 112 | ATGGCCTGTGACTGCACAtacc | 331 -> 352 |
| 06 | reverse | SEQ ID NO: 113 | ACCATTTGGGGGAGGCGAtaac | 290 -> 311 |
| 42 | forward | SEQ ID NO: 114 | TGACTTTGTGTGCCACTGcaac | 100 -> 121 |
| 42 | forward | SEQ ID NO: 115 | ACATCTGGTGATACATATacag | 120 -> 141 |
| 42 | reverse | SEQ ID NO: 116 | CTGGCGTTGTTACCTTAGcctg | 357 -> 378 |
| 43 | forward | SEQ ID NO: 117 | TGTGCCTCTACTGACCCTactg | 108 -> 129 |
| 44 | forward | SEQ ID NO: 118 | CTACACAGTCCCCTCCGTctac | 138 -> 159 |
| 53 | forward | SEQ ID NO: 119 | CAGGAATACAAACATGACTCtttc | 87 -> 109 |
| 53 | reverse | SEQ ID NO: 120 | GCTAGTGGCAACAGGAGGcgac | 290 -> 311 |
| 53 | forward | SEQ ID NO: 121 | CCAGGAATACAAACATGactc | 85 -> 105 |
| 67 | forward | SEQ ID NO: 122 | AAGGAATACCTTAGACATGtgg | 153 -> 174 |
| 67 | forward | SEQ ID NO: 123 | AAGGAATACCTTAGACATGTGgaa | 153 -> 176 |

TABLE 4

| Primer type | SEQ ID NO: | Sequence[2] | Location[1] |
|---|---|---|---|
| forward | SEQ ID NO: 124 | GCACAGGGACATAACAATGG | 6582 -> 6602 |
| forward | SEQ ID NO: 125 | GCGCAGGGCCACAATAATGG | 6582 -> 6602 |
| forward | SEQ ID NO: 126 | GCACAGGGACATAATAATGG | 6582 -> 6602 |
| forward | SEQ ID NO: 127 | GCCCAGGGCCACAACAATGG | 6582 -> 6602 |
| forward | SEQ ID NO: 128 | GCTCAGGGTTTAAACAATGG | 6582 -> 6602 |
| reverse | SEQ ID NO: 129 | CGTCCCAAAGGAAACTGATC | 7014 -> 7034 |
| reverse | SEQ ID NO: 130 | CGACCTAAAGGAAACTGATC | 7014 -> 7034 |
| reverse | SEQ ID NO: 131 | CGTCCAAAAGGAAACTGATC | 7014 -> 7034 |
| reverse | SEQ ID NO: 132 | GCCAAGGGGAAACTGATC | 7014 -> 7032 |
| reverse | SEQ ID NO: 133 | CGTCCCAAAGGATACTGATC | 7014 -> 7034 |
| reverse | SEQ ID NO: 134 | CGTCCAAGGGGATACTGATC | 7014 -> 7034 |
| reverse | SEQ ID NO: 135 | CGACCTAAAGGGAATTGATC | 7014 -> 7034 |
| reverse | SEQ ID NO: 136 | CGACCTAGTGGAAATTGATC | 7014 -> 7034 |

TABLE 4-continued

| Primer type | SEQ ID NO: | Sequence² | Location¹ |
|---|---|---|---|
| reverse | SEQ ID NO: 137 | CGACCAAGGGGATATTGATC | 7014 -> 7034 |
| reverse | SEQ ID NO: 138 | GCCCAACGGAAACTGATC | 7014 -> 7032 |
| reverse | SEQ ID NO: 139 | CGACCCAAGGGAAACTGGTC | 7014 -> 7034 |
| reverse | SEQ ID NO: 140 | CGTCCTAAAGGAAACTGGTC | 7014 -> 7034 |
| forward | SEQ ID NO: 141 | GCGACCCAATGCAAATTGGT | 7015 -> 7035 |
| jkso1 | SEQ ID NO: 142 | CGCCCTAAGGGAAACTGGgt | 7015 -> 7035 |
| jkso2 | SEQ ID NO: 143 | CGCCCTAAGGGAAACTgg | 7014 -> 7034 |

¹Location is relative to HPV16 sequence (gb_vi:nc001526).
²Sequences 124-141 are from Gravitt et al., J. Clin. Microbiol, 2000, Jan., 38(1): 357-61.

TABLE 5

| Strain(s) | type | SEQ ID NO: | Sequence | Location |
|---|---|---|---|---|
| 16, 18, 31, 33, 35, 45, 52, 58, and, 68 | rev. | SEQ ID NO: 144 | GATCTAGATCTGCAGAAAACTTTTC | 439 -> 463 |
| 66 | rev. | SEQ ID NO: 145 | GATCTAGATCTGCAGAAAAgcTgTC | 439 -> 463 |
| 56 | rev. | SEQ ID NO: 146 | GATCTAGATCTGCAGAAAAacTgTC | 439 -> 463 |
| 59 | rev. | SEQ ID NO: 147 | GATCTAGATCTGCAGAAAACcTTTC | 439 -> 463 |
| 31, 33, 35, 45, 59, 39, and 68 | fwd. | SEQ ID NO: 148 | GGACATAACAATGGTATTTGTTGG | 27 -> 50 |
| 18 | fwd. | SEQ ID NO: 149 | GGACATAACAATGGTATTTGcTGG | 27-> 50 |
| 51, 56, and 58 | fwd. | SEQ ID NO: 150 | GGACATAACAATGGcATTTGcTGG | 27 -> 50 |
| 66 and 52 | fwd. | SEQ ID NO: 151 | GGACAcAACAATGGcATaTGcTGG | 27-> 50 |
| 16 and 52 | fwd. | SEQ ID NO: 152 | GGACATAACAATGGcATTTGTTGG | 27-> 50 |
| 59 | fwd. | SEQ ID NO: 153 | GGtttaAACAATGGTATTTGTTGG | 27-> 50 |
| — | rev. | SEQ ID NO: 154 | TCTAGATCARTTTCCTTTGGGA | 156 -> 178 |

In certain embodiments, the primers (e.g., SEQ ID NOs: 1-123 and 142-154) are use for HPV typing. In some embodiments, the primers are used to amplify HPV sequences in a sample. In particular embodiments, the primers are used for sequencing.

The primers of the present invention have been configured to amplify the largest number of HPV types with the fewest number of primers in the mix. In general, primer are tailored to conserved regions of the HPV genome, and are configured to not interact with each other (e.g., by forming primer dimers).

In Table 3, SEQ ID NOs:124-141 are from Gravitt et al., J. Clin. Microbiol, 2000, Jan., 38(1):357-61 (herein incorporated by reference). This set of PGMY primers from Gravitt et al. was shown to be able to type about 42 HPV types. The addition of primer SEQ ID NO:142 to the PGMY set of primers allows the number of HPV types to be typed to be expanded beyond 42 (e.g., up to about 65). In certain embodiment, the addition of primer SEQ ID NO:143 to the set of PGMY set of primers also allows the number of HPV types to be expanded beyond 42.

In certain embodiments, the primers of the present invention are used to amplify a portion of the HPV genome, and then the amplicons are contacted with a nucleic acid detection assay, such as the INVADER assay, in order to determine what type is in the sample. The present invention is not limited by the type of nucleic acid detection assay that is employed. The INVADER assay is detailed below as one exemplary type of assay that could be employed.

When two strands of nucleic acid, or oligonucleotides, both hybridize to a target nucleic acid strand such that they form an overlapping invasive cleavage structure, as described below, invasive cleavage can occur. Through the interaction of a cleavage agent (e.g., a 5' nuclease) and the upstream oligonucleotide, the cleavage agent can be made to cleave the downstream oligonucleotide at an internal site in such a way that a distinctive fragment is produced. Such embodiments have been termed the INVADER assay (Third Wave Technologies) and are described in U.S. Pat. Nos. 5,846,717, 5,985,557, 5,994,069, 6,001,567, and 6,090,543, WO 97/27214 WO 98/42873, Lyamichev et al., Nat. Biotech., 17:292 (1999), Hall et al., PNAS, USA, 97:8272 (2000), each of which is herein incorporated by reference in their entirety for all purposes).

The INVADER assay detects hybridization of probes to a target by enzymatic cleavage of specific structures by structure specific enzymes (See, INVADER assays, Third Wave Technologies; See e.g., U.S. Pat. Nos. 5,846,717; 6,090,543; 6,001,567; 5,985,557; 6,090,543; 5,994,069; Lyamichev et al., Nat. Biotech., 17:292 (1999), Hall et al., PNAS, USA, 97:8272 (2000), WO97/27214 and WO98/42873, each of which is herein incorporated by reference in their entirety for all purposes).

The INVADER assay detects specific DNA and RNA sequences by using structure-specific enzymes (e.g. FEN endonucleases) to cleave a complex formed by the hybridization of overlapping oligonucleotide probes. Elevated temperature and an excess of one of the probes enable multiple probes to be cleaved for each target sequence present without temperature cycling. In some embodiments, these cleaved probes then direct cleavage of a second labeled probe. The secondary probe oligonucleotide can be 5'-end labeled with fluorescein that is quenched by an internal dye. Upon cleavage, the de-quenched fluorescein labeled product may be detected using a standard fluorescence plate reader.

The INVADER assay detects specific mutations and SNPs in unamplified, as well as amplified, RNA and DNA including genomic DNA. In some embodiments, the INVADER assay uses two cascading steps (a primary and a secondary reaction) both to generate and then to amplify the target-specific signal. For convenience, the alleles in the following discussion are described as wild-type (WT) and mutant (MT), even though this terminology does not apply to all genetic variations. In the primary reaction, the WT primary probe and the INVADER oligonucleotide hybridize in tandem to the target nucleic acid to form an overlapping structure. An unpaired "flap" is included on the 5' end of the WT primary probe. A structure-specific enzyme (e.g. the CLEAVASE enzyme, Third Wave Technologies) recognizes the overlap and cleaves off the unpaired flap, releasing it as a target-specific product. In the secondary reaction, this cleaved product serves as an INVADER oligonucleotide on the WT fluorescence resonance energy transfer (WT-FRET) probe to again create the structure recognized by the structure specific enzyme. When the two dyes on a single FRET probe are separated by cleavage, a detectable fluorescent signal above background fluorescence is produced. Consequently, cleavage of this second structure results in an increase in fluorescence, indicating the presence of the WT allele (or mutant allele if the assay is configured for the mutant allele to generate the detectable signal). In some embodiments, FRET probes having different labels (e.g. resolvable by difference in emission or excitation wavelengths, or resolvable by time-resolved fluorescence detection) are provided for each allele or locus to be detected, such that the different alleles or loci can be detected in a single reaction. In such embodiments, the primary probe sets and the different FRET probes may be combined in a single assay, allowing comparison of the signals from each allele or locus in the same sample.

If the primary probe oligonucleotide and the target nucleotide sequence do not match perfectly at the cleavage site (e.g., as with the MT primary probe and the WT target, the overlapped structure does not form and cleavage is suppressed. The structure specific enzyme (e.g., CLEAVASE VIII enzyme, Third Wave Technologies) used cleaves the overlapped structure more efficiently (e.g. at least 340-fold) than the non-overlapping structure, allowing excellent discrimination of the alleles.

The probes turn over without temperature cycling to produce many signals per target (i.e., linear signal amplification). Similarly, each target-specific product can enable the cleavage of many FRET probes.

The primary INVADER assay reaction is directed against the target DNA (or RNA) being detected. The target DNA is the limiting component in the first invasive cleavage, since the INVADER and primary probe are supplied in molar excess. In the second invasive cleavage, it is the released flap that is limiting. When these two cleavage reactions are performed sequentially, the fluorescence signal from the composite reaction accumulates linearly with respect to the target DNA amount.

In certain embodiments, the INVADER assay, or other nucleotide detection assays, are performed with accessible site designed oligonucleotides and/or bridging oligonucleotides. Such methods, procedures and compositions are described in U.S. Pat. No. 6,194,149, WO9850403, and WO0198537, all of which are specifically incorporated by reference in their entireties.

In certain embodiments, the target nucleic acid sequence is amplified with the primers of the present invention prior to detection (e.g. such that synthetic nucleic acid is generated). In some embodiments, the target nucleic acid comprises genomic DNA. In other embodiments, the target nucleic acid comprises synthetic DNA or RNA. In some preferred embodiments, synthetic DNA within a sample is created using a purified polymerase. In some preferred embodiments, creation of synthetic DNA using a purified polymerase comprises the use of PCR. In other preferred embodiments, creation of synthetic DNA using a purified DNA polymerase, suitable for use with the methods of the present invention, comprises use of rolling circle amplification, (e.g., as in U.S. Pat. Nos. 6,210,884, 6,183,960 and 6,235,502, herein incorporated by reference in their entireties). In other preferred embodiments, creation of synthetic DNA comprises copying genomic DNA by priming from a plurality of sites on a genomic DNA sample. In some embodiments, priming from a plurality of sites on a genomic DNA sample comprises using short (e.g., fewer than about 8 nucleotides) oligonucleotide primers. In other embodiments, priming from a plurality of sites on a genomic DNA comprises extension of 3' ends in nicked, double-stranded genomic DNA (i.e., where a 3' hydroxyl group has been made available for extension by breakage or cleavage of one strand of a double stranded region of DNA). Some examples of making synthetic DNA using a purified polymerase on nicked genomic DNAs, suitable for use with the methods and compositions of the present invention, are provided in U.S. Pat. Nos. 6,117,634, issued Sep. 12, 2000, and U.S. Pat. No. 6,197,557, issued Mar. 6, 2001, and in PCT application WO 98/39485, each incorporated by reference herein in their entireties for all purposes.

All publications and patents mentioned in the above specification are herein incorporated by reference as if expressly set forth herein. Various modifications and variations of the described assays of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in relevant fields are intended to be within the scope of the following claims.

We claim:

1. A composition configured to hybridize to target nucleic acids from a plurality of different HPV types, said composition comprising an isolated nucleic acid sequence, wherein the nucleotide sequence of said isolated nucleic acid sequence consists of SEQ ID NO:142 or SEQ ID NO:143.

2. The composition of claim 1, further comprising a second isolated nucleic acid sequence different from said isolated nucleic acid sequence, wherein the nucleotide sequence of said second isolated nucleic acid sequence consists of SEQ ID NO:142 or SEQ ID NO:143.

3. The composition of claim 1, further comprising at least 20 additional isolated nucleic acid sequences, wherein the nucleotide sequences of said additional isolated nucleic acid sequences each consist of a nucleotide sequence shown in SEQ ID NOs:1-123 and 142-154.

4. A kit comprising a composition configured to hybridize to target nucleic acids from a plurality of different HPV types, said composition comprising an isolated nucleic acid sequence, wherein the nucleotide sequence of said isolated nucleic acid sequence consists of SEQ ID NO:142 or SEQ ID NO:143.

5. The kit of claim 4, wherein said composition further comprises a second isolated nucleic acid sequence different from said isolated nucleic acid sequence, wherein the nucleotide sequence of said second isolated nucleic acid sequence consists of SEQ ID NO:142 or SEQ ID NO:143.

6. The kit of claim 4, further comprising at least 20 additional isolated nucleic acid sequences, wherein the nucleotide sequences of said additional isolated nucleic acid sequences each consist of a nucleotide sequence shown in SEQ ID NOs:1-123 and 142-154.

7. A method for detecting at least one HPV sequence in a sample, comprising using a composition configured to hybridize to target nucleic acids from a plurality of different HPV types, said composition comprising an isolated nucleic acid sequence, wherein the nucleotide sequence of said isolated nucleic acid sequence consist of SEQ ID NO:142 or SEQ ID NO:143.

8. The method of claim 7, wherein said detecting allows typing of said HPV sequence.

9. The method of claim 7, wherein said using comprises sequencing with said nucleic acid sequence.

10. The method of claim 7, wherein said using comprises amplifying said HPV sequence with said nucleic acid sequence.

* * * * *